(12) United States Patent
Runco et al.

(10) Patent No.: US 7,887,541 B2
(45) Date of Patent: Feb. 15, 2011

(54) SPINAL ROD REDUCTION INSTRUMENTS AND METHODS FOR USE

(75) Inventors: Thomas J. Runco, Canton, MA (US); Richard W. Fournier, New Bedford, MA (US)

(73) Assignee: Depuy Spine, Inc., Raynham, MA (US)

( * ) Notice: Subject to any disclaimer, the term of this patent is extended or adjusted under 35 U.S.C. 154(b) by 86 days.

(21) Appl. No.: 11/828,652

(22) Filed: Jul. 26, 2007

(65) Prior Publication Data

US 2009/0030419 A1    Jan. 29, 2009

(51) Int. Cl.
*A61F 5/00* (2006.01)
(52) U.S. Cl. .................... 606/86 A; 606/99; 606/279
(58) Field of Classification Search ............. 606/86 A, 606/86 B, 86 R, 99, 103, 246–279; A61F 5/00
See application file for complete search history.

(56) References Cited

U.S. PATENT DOCUMENTS

| | | |
|---|---|---|
| 410,780 A | 9/1889 | Cahn |
| 1,470,313 A | 10/1923 | Woolen |
| 1,628,144 A | 5/1927 | Herrmann |
| 1,709,766 A | 4/1929 | Bolton |
| 1,889,330 A | 11/1932 | Humes et al. |
| 1,925,385 A | 9/1933 | Humes et al. |
| 2,248,054 A | 7/1941 | Becker |
| 2,248,057 A | 7/1941 | Bond |
| 2,291,413 A | 7/1942 | Siebrandt |
| 2,370,407 A | 2/1945 | McCartney |
| 2,800,820 A | 7/1957 | Retterath |
| 3,960,147 A | 6/1976 | Murray |
| 4,237,875 A | 12/1980 | Termanini |
| 4,271,836 A | 6/1981 | Bacal et al. |
| 4,411,259 A | 10/1983 | Drummond |
| 4,445,513 A | 5/1984 | Ulrich |

(Continued)

FOREIGN PATENT DOCUMENTS

DE    4238339    5/1994

(Continued)

OTHER PUBLICATIONS

International Search Report (PCT/US2008/068515) dated Jan. 2, 2009.

(Continued)

*Primary Examiner*—Eduardo C Robert
*Assistant Examiner*—Lynnsy Schneider

(57) ABSTRACT

Methods and devices are provided for reducing a spinal fixation element into a spinal implant element. In one exemplary embodiment, a spinal rod reduction device is provided for reducing a spinal fixation element into a spinal implant element. The spinal rod reduction device can include a fastener engaging member for engaging at least a portion a spinal implant element, a reduction member for engaging at least a portion of a spinal fixation element, and a handle assembly mated to the reduction member. The handle assembly can be designed in such a way that actuation of the handle assembly causes movement of the reduction member relative to the fastener engaging member and the movement of the reduction member reduces the spinal fixation element into the spinal implant element. Two different styles of spinal rod reduction devices are discussed in detail. Various techniques are also provided for reducing a spinal fixation element into a spinal implant element.

25 Claims, 12 Drawing Sheets

U.S. PATENT DOCUMENTS

| | | | |
|---|---|---|---|
| 4,655,223 A | 4/1987 | Kim | |
| 4,809,695 A | 3/1989 | Gwathmey et al. | |
| 4,896,661 A | 1/1990 | Bogert | |
| 5,014,407 A | 5/1991 | Boughten | |
| 5,020,519 A | 6/1991 | Hayes et al. | |
| 5,364,397 A | 11/1994 | Hayes et al. | |
| 5,391,170 A | 2/1995 | McGuire et al. | |
| 5,429,641 A | 7/1995 | Gotfried et al. | |
| 5,484,440 A | 1/1996 | Allard | |
| 5,545,165 A | 8/1996 | Biedermann et al. | |
| 5,551,320 A | 9/1996 | Horobec | |
| 5,616,143 A | 4/1997 | Schlapfer et al. | |
| 5,649,931 A | 7/1997 | Bryant et al. | |
| 5,697,933 A | 12/1997 | Gundlapalli et al. | |
| 5,707,371 A | 1/1998 | Metz-Stavenhagen et al. | |
| 5,720,751 A | 2/1998 | Jackson | |
| 5,725,532 A | 3/1998 | Shoemaker | |
| 5,746,757 A | 5/1998 | McGuire | |
| 5,782,831 A | 7/1998 | Sherman et al. | |
| 5,810,878 A | 9/1998 | Burel et al. | |
| 5,910,141 A | 6/1999 | Morrison et al. | |
| 5,951,564 A | 9/1999 | Schroder et al. | |
| 6,010,509 A | 1/2000 | Delgado | |
| 6,036,692 A | 3/2000 | Burel et al. | |
| 6,099,528 A | 8/2000 | Saurat et al. | |
| 6,123,707 A | 9/2000 | Wagner | |
| 6,139,549 A | 10/2000 | Keller | |
| 6,183,472 B1 | 2/2001 | Lutz et al. | |
| 6,210,330 B1 | 4/2001 | Tepper et al. | |
| 6,251,112 B1 | 6/2001 | Jackson | |
| 6,258,090 B1 | 7/2001 | Jackson | |
| 6,371,973 B1 | 4/2002 | Tepper et al. | |
| 6,440,133 B1 | 8/2002 | Beale et al. | |
| 6,440,142 B1 | 8/2002 | Ralph et al. | |
| 6,511,484 B2 | 1/2003 | Torode et al. | |
| 6,530,929 B1 | 3/2003 | Justis et al. | |
| 6,589,249 B2 | 7/2003 | Sater et al. | |
| 6,648,888 B1 | 11/2003 | Shluzas | |
| 6,660,006 B2 | 12/2003 | Markworth et al. | |
| 6,726,692 B2 | 4/2004 | Bette et al. | |
| 6,743,231 B1 | 6/2004 | Gray et al. | |
| 6,746,449 B2 | 6/2004 | Jones et al. | |
| 6,752,832 B2 | 6/2004 | Neumann | |
| 6,755,829 B1 | 6/2004 | Bono et al. | |
| 6,790,208 B2 | 9/2004 | Oribe et al. | |
| 6,790,209 B2 * | 9/2004 | Beale et al. | 606/86 A |
| 6,827,722 B1 | 12/2004 | Schoenefeld | |
| 7,156,849 B2 | 1/2007 | Dunbar | |
| 7,179,254 B2 | 2/2007 | Pendekanti | |
| 7,179,261 B2 | 2/2007 | Sicvol | |
| 7,278,995 B2 | 10/2007 | Nichols et al. | |
| 7,320,689 B2 | 1/2008 | Keller | |
| 7,491,207 B2 | 2/2009 | Keyer et al. | |
| 7,527,638 B2 | 5/2009 | Anderson | |
| 7,572,281 B2 | 8/2009 | Runco | |
| 7,666,188 B2 | 2/2010 | Anderson | |
| 7,708,763 B2 | 5/2010 | Selover | |
| 2001/0029376 A1 | 10/2001 | Sater | |
| 2002/0095153 A1 | 7/2002 | Jones et al. | |
| 2003/0028195 A1 | 2/2003 | Bette | |
| 2003/0083747 A1 | 5/2003 | Winterbottom et al. | |
| 2003/0125750 A1 | 7/2003 | Zwirnmann et al. | |
| 2003/0149438 A1 | 8/2003 | Nichols et al. | |
| 2003/0191370 A1 | 10/2003 | Phillips | |
| 2003/0199872 A1 | 10/2003 | Markworth et al. | |
| 2003/0225408 A1 | 12/2003 | Nichols et al. | |
| 2004/0036254 A1 | 2/2004 | Patton | |
| 2004/0049191 A1 | 3/2004 | Markworth et al. | |
| 2004/0147936 A1 | 7/2004 | Rosenberg et al. | |
| 2004/0147937 A1 | 7/2004 | Dunbar et al. | |
| 2004/0172057 A1 | 9/2004 | Guillebon | |
| 2004/0176779 A1 | 9/2004 | Casutt et al. | |
| 2004/0220567 A1 | 11/2004 | Eisermann et al. | |
| 2004/0254576 A1 | 12/2004 | Dunbar | |
| 2004/0267275 A1 | 12/2004 | Cournoyer et al. | |
| 2005/0015095 A1 | 1/2005 | Keller | |
| 2005/0033299 A1 * | 2/2005 | Shluzas | 606/61 |
| 2005/0055031 A1 | 3/2005 | Lim | |
| 2005/0059969 A1 | 3/2005 | McKinley | |
| 2005/0079909 A1 | 4/2005 | Singhaseni | |
| 2005/0090824 A1 | 4/2005 | Shluzas et al. | |
| 2005/0131408 A1 | 6/2005 | Sicvol et al. | |
| 2005/0131420 A1 | 6/2005 | Techiera et al. | |
| 2005/0131422 A1 | 6/2005 | Anderson | |
| 2005/0143749 A1 | 6/2005 | Zalenski et al. | |
| 2005/0149036 A1 | 7/2005 | Varieur et al. | |
| 2005/0149048 A1 | 7/2005 | Leport et al. | |
| 2005/0149053 A1 | 7/2005 | Varieur et al. | |
| 2005/0192570 A1 | 9/2005 | Jackson | |
| 2005/0192579 A1 | 9/2005 | Jackson | |
| 2005/0228392 A1 | 10/2005 | Keyer et al. | |
| 2005/0261702 A1 | 11/2005 | Oribe et al. | |
| 2006/0009775 A1 | 1/2006 | Dec et al. | |
| 2006/0025768 A1 | 2/2006 | Iott et al. | |
| 2006/0036254 A1 | 2/2006 | Lim | |
| 2006/0036260 A1 * | 2/2006 | Runco et al. | 606/99 |
| 2006/0074418 A1 | 4/2006 | Jackson | |
| 2006/0079909 A1 | 4/2006 | Runco et al. | |
| 2006/0089651 A1 * | 4/2006 | Trudeau et al. | 606/86 |
| 2006/0095035 A1 | 5/2006 | Jones et al. | |
| 2006/0111730 A1 | 5/2006 | Hay | |
| 2006/0166534 A1 | 7/2006 | Brumfield et al. | |
| 2006/0166535 A1 | 7/2006 | Brumfield et al. | |
| 2006/0293692 A1 | 12/2006 | Whipple et al. | |
| 2007/0093849 A1 | 4/2007 | Jones et al. | |
| 2007/0129731 A1 | 6/2007 | Sicvol | |
| 2007/0161998 A1 | 7/2007 | Whipple | |
| 2007/0167954 A1 | 7/2007 | Sicvol | |
| 2007/0173831 A1 | 7/2007 | Abdou | |
| 2007/0213722 A1 * | 9/2007 | Jones et al. | 606/61 |
| 2007/0233097 A1 | 10/2007 | Anderson | |
| 2007/0260261 A1 | 11/2007 | Runco et al. | |
| 2008/0077134 A1 | 3/2008 | Dziedzic | |
| 2008/0077135 A1 | 3/2008 | Stad et al. | |
| 2008/0243190 A1 | 10/2008 | Dziedzic | |
| 2008/0255574 A1 | 10/2008 | Dye | |
| 2009/0030419 A1 | 1/2009 | Runco | |
| 2009/0030420 A1 | 1/2009 | Runco | |
| 2009/0054902 A1 | 2/2009 | Mickiewicz et al. | |
| 2009/0082811 A1 | 3/2009 | Stad | |
| 2009/0088764 A1 | 4/2009 | Stad | |
| 2009/0138056 A1 | 5/2009 | Anderson | |
| 2009/0143828 A1 | 6/2009 | Stad | |
| 2010/0137915 A1 | 6/2010 | Anderson | |

FOREIGN PATENT DOCUMENTS

| | | |
|---|---|---|
| DE | 29806563 U1 | 6/1998 |
| EP | 0948939 A2 | 10/1999 |
| EP | 1574175 | 9/2005 |
| EP | 1648320 | 4/2006 |
| EP | 1796564 | 6/2007 |
| FR | 2677242 | 12/1992 |
| FR | 2729291 | 1/1995 |
| WO | 9621396 A1 | 7/1996 |

OTHER PUBLICATIONS

U.S. Appl. No. 11/539,496, Dziedzic et al.
U.S. Appl. No. 11/756,318, Runco et al.
Sofamor Introducteur—Contreur De Tige, Jun. 1994.
Sofamor, "Introducteur—Contreur De Tige" (schematic drawings), Jan. 1, 1994.

* cited by examiner

SPINAL ROD REDUCTION INSTRUMENTS AND METHODS FOR USE

FIELD

Devices and methods are provided for use in spinal surgery, and in particular spinal rod reduction devices and methods for using the same are provided.

BACKGROUND

Spinal fixation devices are used in orthopedic surgery to align and/or fix a desired relationship between adjacent vertebral bodies. Such devices typically include a spinal fixation element, such as a relatively rigid fixation rod, that is coupled to adjacent vertebrae by attaching the element to various anchoring devices, such as hooks, bolts, wires, or screws. The fixation rods can have a predetermined contour that has been designed according to the properties of the target implantation site, and once installed, the instrument holds the vertebrae in a desired spatial relationship, either until desired healing or spinal fusion has taken place, or for some longer period of time.

Spinal fixation devices can be anchored to specific portions of the vertebra. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped slot formed in the head. A set-screw, plug, or similar type of fastening mechanism, is used to lock the fixation rod into the rod-receiving head of the pedicle screw. In use, the shank portion of each screw is threaded into a vertebra, and once properly positioned, a fixation rod is seated through the rod-receiving member of each screw and the rod is locked in place by tightening a cap or other fastener mechanism to securely interconnect each screw and the fixation rod.

While current spinal fixation systems have proven effective, difficulties have been encountered in mounting rods into the rod-receiving member of various fixation devices. In particular, it can be difficult to align and seat the rod into the rod receiving portion of adjacent fixation devices due to the positioning and rigidity of the vertebra into which the fixation device is mounted. Thus, the use of a spinal rod reduction device, also sometimes referred to as a spinal rod approximator, is often required in order to grasp the head of the fixation device and reduce the rod into the rod-receiving head of the fixation device.

While several rod reduction devices are known in the art, some tend to be difficult and very time-consuming to use. Accordingly, there is a need for improved rod reduction devices and methods for seating a spinal rod, or other spinal fixation element, into one or more spinal implants or fasteners.

SUMMARY

Methods and devices are provided for reducing a spinal fixation element into a fastener to allow the spinal fixation element to be locked in the fastener. In one embodiment, a spinal rod reduction device is provided and includes a fastener engaging member having first and second jaws adapted to engage at least a portion of a fastener. In an exemplary embodiment, the first and second jaws are spaced a distance apart from one another to define an opening therebetween. The first and second jaws can also include a mating element formed thereon and adapted to engage a fastener. The device can further include a first arm fixedly coupled to the fastener engaging member, and a second arm pivotally coupled to the first arm. A linkage can be pivotally coupled to the second arm and in an exemplary embodiment the linkage extends transverse to a longitudinal axis of the fastener engaging member. The device can also include a reduction member pivotally coupled to the linkage such that pivotal movement of the second arm relative to the first arm is effective to move the reduction member along the longitudinal axis of the fastener engaging member to reduce a spinal rod extending between the first and second jaws into a fastener engaged by the first and second jaws. In one embodiment, the reduction member can include a sleeve disposed around the first and second jaws and adapted to lock the first and second jaws in a fixed position. In another embodiment, the reduction member can include first and second legs having rod-receiving recesses formed in a distal-most end thereof. In an exemplary embodiment, the second arm can be movable between an initial position in which the reduction member is positioned proximal of a distal end of the first and second jaws, and a final position in which the reduction member is positioned adjacent to the distal end of the first and second jaws. The linkage can be adapted to be substantially aligned with the longitudinal axis of the fastener engaging member when the second arm is in the final position.

The device can also have a variety of other configurations. For example, the first arm can include a proximal portion that extends substantially parallel to the longitudinal axis of the fastener engaging member, and a distal portion that extends transverse to the proximal portion and that is mated to the fastener engaging member. The device can also include a linear pathway that extends through the fastener engaging member, the first arm, and the second arm for receiving a rod retainer for mating to a fastener engaged by the fastener engaging member.

In yet another embodiment, the device can include a locking mechanism coupled to at least one of the first and second arms and effective to maintain the first and second arms in a desired fixed position relative to one another. For example, the locking mechanism can be in the form of at least one notch located on one of the first and second arms and at least one protrusion located on the other one of the first and second arms and adapted to engage the at least one notch. The locking mechanism can also be adjustable to allow the first and second arms to be maintained at a desired fixed position relative to one another.

In another embodiment, a spinal rod reduction device is provided and includes a hollow elongate member having a handle formed on a proximal end thereof and extending substantially parallel to a longitudinal axis of the hollow elongate member, and first and second jaws formed on a distal end thereof and adapted to move apart to engage a fastener therebetween. A reduction member is slidably coupled to the hollow elongate member and it is adapted to distally advance a spinal rod extending between the first and second jaws into the fastener engaged by the first and second jaws. The device can also include a linkage assembly pivotally coupled to the handle and the reduction member and adapted to advance the reduction member relative to the first and second jaws. In one embodiment, the reduction member can include a sleeve disposed around the hollow elongate member. The sleeve can be movable between an initial position in which the first and second jaws are free to flex relative to one another to receive a fastener therebetween, and a final position in which the first and second jaws are locked in a fixed position relative to one another to engage a fastener therebetween.

While the linkage assembly can have a variety of configurations, in an exemplary embodiment at least a portion of the linkage assembly extends transverse to the longitudinal axis of the hollow elongate member in a first position, and it extends substantially parallel to the longitudinal axis of the hollow elongate member in a second position. The linkage assembly can include, for example, an actuator pivotally coupled to the handle and at least one linkage extending between the actuator and the reduction member. The device can also optionally include a locking mechanism coupled to the handle and effective to maintain the reduction member in a desired fixed position relative to the hollow elongate member.

In other aspects, a method for reducing a spinal rod into a bone anchor is provided and includes positioning a fastener between first and second jaws formed on a fastener engaging member, and pivoting a movable arm toward a stationary arm fixedly mated to the fastener engaging member to pivot a linkage coupled to the movable arm from a first position in which the linkage extends transverse to a longitudinal axis of the fastener engaging member, to a second position in which the linkage extends substantially parallel to the longitudinal axis of the fastener engaging member. The linkage can advance a reduction member toward the fastener as the linkage moves from the first position to the second position to advance a spinal rod extending between the opposed jaws into the fastener. The method can also include delivering a rod retainer through a pathway extending through the fastener engaging member, and applying the rod retainer to the fastener to lock the spinal rod in the fastener. In an exemplary embodiment, the pathway is a linear pathway extending between the movable arm and the stationary arm and extending through the fastener engaging member.

In another embodiment, when the movable arm is pivoted toward the stationary arm, the reduction member can be advanced over the first and second jaws into a locked position to lock the first and second jaws in a fixed position relative to one another to thereby engage the fastener between the first and second jaws. The movable arm can also be maintained in the second position by a locking mechanism that extends between the movable arm and the stationary arm.

In yet another embodiment, a spinal rod reduction device is provided and includes a fastener engaging member having first and second jaws adapted to engage at least a portion of a fastener, and a housing fixedly coupled to the fastener engaging member. In an exemplary embodiment, the housing is offset from and extends substantially parallel to the longitudinal axis of the fastener engaging member. The device can also include a reduction member coupled to a distal end of a pusher member, and a handle assembly coupled to a proximal end of the pusher member and adapted to move the pusher member parallel to a longitudinal axis of the fastener engaging member to cause the reduction member to reduce a spinal rod extending between the first and second jaws into a fastener engaged by the first and second jaws. In one embodiment, the handle assembly can be an actuator pivotally coupled to a handle formed on a proximal end of the housing. A biasing element can optionally be disposed between the actuator and the handle for biasing the actuator to one of an open and closed position. The biasing element can be, for example, a leaf spring. The device can also include a locking mechanism coupled to the handle assembly and adapted to maintain the reduction member in a desired fixed position relative to the first and second jaws. The locking mechanism can be, for example, at least one notch formed in the pusher member, and at least one protrusion located on the handle assembly and adapted to engage the at least one notch. In another embodiment, a locking mechanism can be coupled to the housing and it can be adapted to selectively engage the pusher member to maintain the pusher in a desired fixed position relative to the housing.

In yet another embodiment, a spinal rod reduction device is provided and includes a hollow elongate member having a distal end with opposed arms adapted to engage a fastener therebetween, a housing coupled to the hollow elongate member, and a pusher slidably disposed through the housing and having a reduction member formed on a distal end thereof and disposed around the hollow elongate member. The reduction member can be adapted to reduce a spinal rod extending between the opposed arms into a fastener engaged by the opposed arms as the pusher is slidably advanced relative to the housing. The device can further include a handle assembly coupled to the housing and the pusher and adapted to move the pusher relative to the housing. The handle assembly can be, for example, a first handle coupled to the housing and a second handle coupled to the pusher. The first and second handles can be pivotally coupled to one another. In one exemplary embodiment, the handle assembly can extend transverse to a longitudinal axis of the housing and the pusher. In another embodiment, the housing can be coupled to an outer sidewall of the hollow elongate member.

In other aspects, a method for reducing a spinal rod into a bone anchor is provided and includes positioning a fastener, such as a bone screw implanted in a vertebra, between first and second jaws formed on a fastener engaging member. A pusher member can be advanced through a housing coupled to the fastener engaging member to advance a reduction member coupled to a distal end of the pusher member toward the fastener to reduce a spinal rod extending between the opposed jaws into the fastener. The reduction member can be disposed around the first and second jaws such that the reduction member locks the jaws in a fixed position as the reduction member is advanced toward the fastener. In an exemplary embodiment, the pusher member is advanced by pivoting an actuator coupled to the pusher member toward a handle coupled to the housing. The actuator can optionally be maintained in a desired fixed position by a locking mechanism that extends between the actuator and the handle. In other aspects, the method can also include delivering a rod retainer through a pathway formed in the fastener engaging member, and applying the rod retainer to the fastener to lock the spinal rod in the fastener.

BRIEF DESCRIPTION OF THE DRAWINGS

The exemplary embodiments disclosed herein will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present devices and methods is defined solely by the claims. The features illustrated or described in connection with one exemplary embodiment may be combined with the features of other embodiments. Such modifications and variations are intended to be included within the scope of the present devices and methods.

Methods and devices are provided for reducing a spinal fixation element, such as a spinal rod, into a fastener, such as a bone screw. The reduction device can have a variety of configurations, but in general the device is preferably effective to manipulate a spinal fixation element into a fastener to allow the fixation element to be mated to and locked into the fastener. In one exemplary embodiment, the device can include a fastener engaging member that is adapted to engage at least a portion of a fastener, a reduction member that is movably coupled to the fastener engaging member, and a handle assembly coupled to the reduction member and that is effective to cause the reduction member to reduce a spinal fixation element into the fastener.

A person skilled in the art will appreciate that, although the spinal rod reduction methods and devices disclosed herein are described as being used in the spinal area of the body, the methods and devices can be used in any situation requiring the reduction of one element into another element, whether it be located in the spinal area of the body, somewhere else in the body, or otherwise. A person skilled in the art will also appreciate that the spinal rod reduction methods and devices can have a variety of configurations to allow for use in conjunction with minimally-invasive techniques or conventional surgical procedures. Furthermore, with particular reference to use in the spinal or vertebral area of the body, although the description provided herein describes the spinal fixation element as a spinal rod and the fastener as a bone screw, a person skilled in the art will appreciate that the spinal fixation element and the fastener are not limited to the illustrated embodiments and that the device can be used with a variety of spinal fixation elements, spinal implants, fasteners, and other surgical devices.

Figure 1:
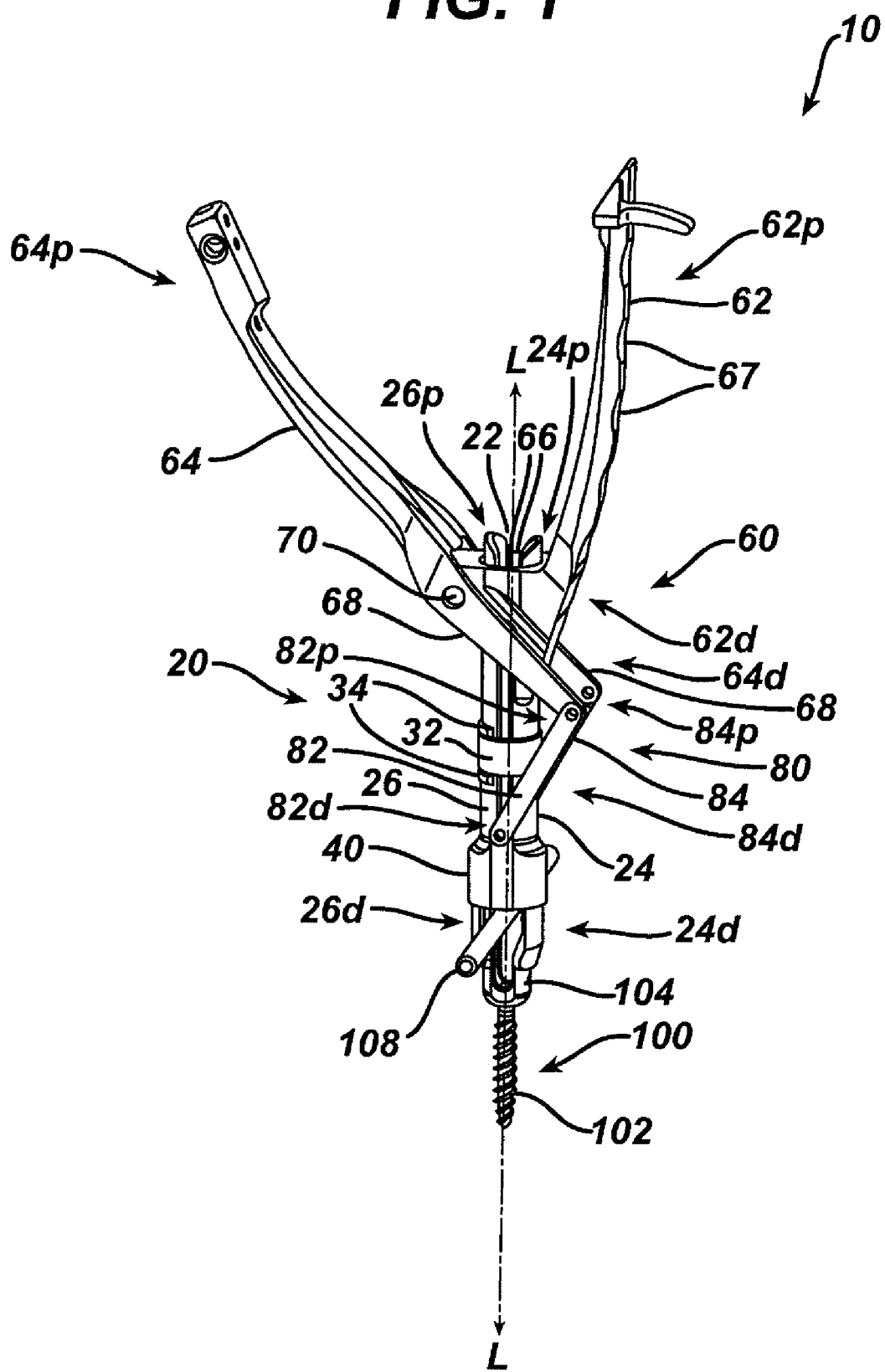
FIG. 1 is a side perspective view of one exemplary embodiment of a spinal rod reduction device in an initial position.
Figure 2:
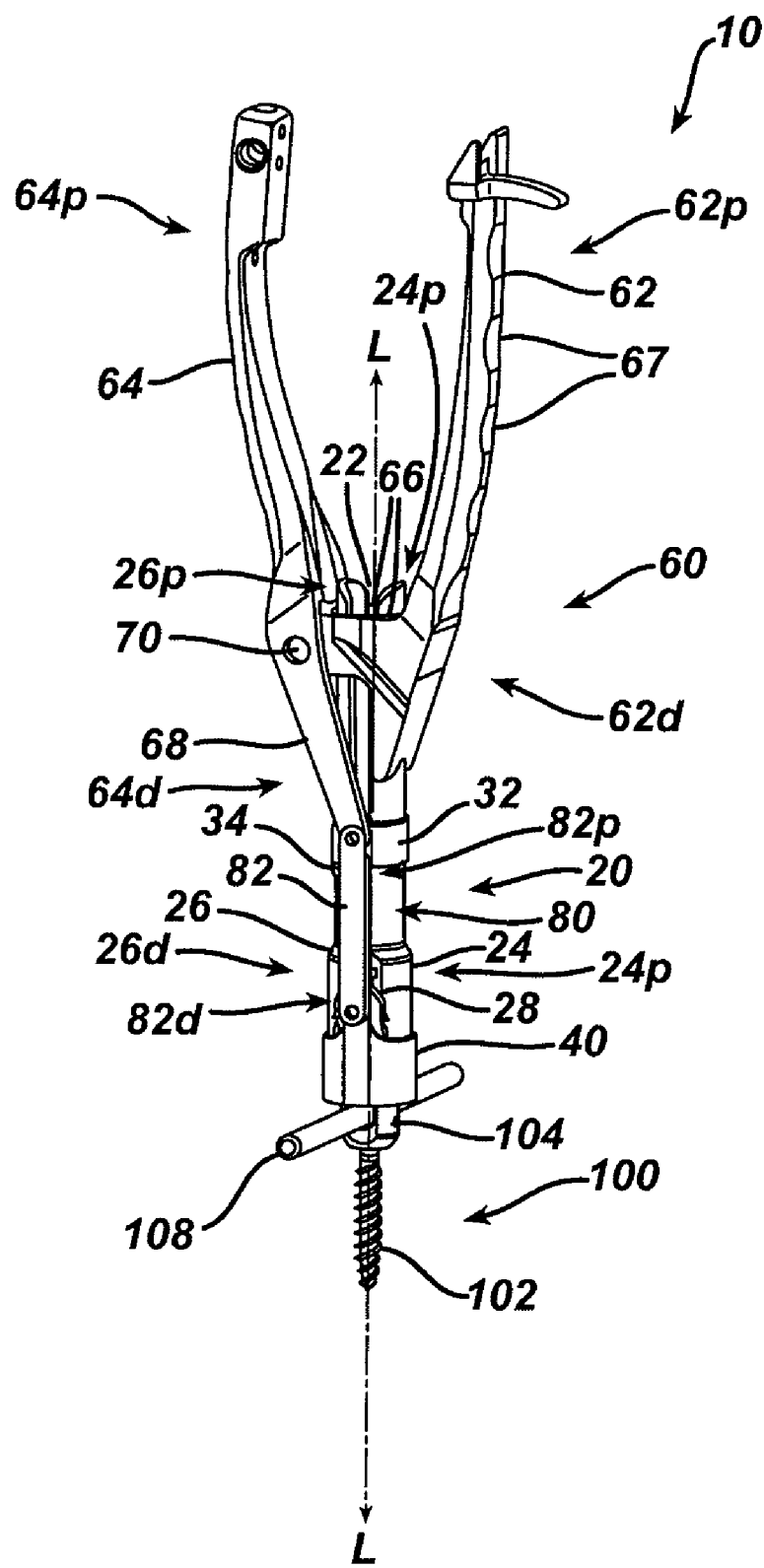
FIG. 2 is a side perspective view of the device of FIG. 1 in a final position.

FIGS. 1 and 2 illustrate one exemplary embodiment of a spinal rod reduction device 10. As shown, the device 10 generally includes a fastener engaging member 20 adapted to engage at least a portion of a fastener, a reduction member 40 movably coupled to the fastener engaging member 20, and a handle assembly 60 mated to the reduction member 40 and adapted to move the reduction member 40 relative to the fastener engaging member 20 to reduce a spinal fixation element into a fastener engaged by the fastener engaging member 20.

As explained above, various fasteners and spinal fixation elements known in the art can be used, however FIGS. 1 and 2 illustrate one exemplary embodiment of a fastener and a spinal fixation element that can be used with the rod reduction devices disclosed herein. As shown, the fastener is in the form of a bone screw 100 having a threaded shank 102 and a rod-receiving head 104. The threaded shank 102 can be adapted to be threaded into bone and the rod-receiving head 104 can be adapted to receive a spinal fixation element, such as a spinal rod 108. In the illustrated embodiment, the rod-receiving head 104 includes opposed arms that define a u-shaped receiving portion for seating the spinal rod 108. The rod-receiving head 104 can also include mating features formed thereon to facilitate mating with the fastener engaging member 20. While various mating features can be used, in one exemplary embodiment the rod-receiving head 104 includes one or more detents formed in a proximal portion thereof for receiving one or more projections formed on the fastener engaging member 20, as will be discussed in more detail below. Other exemplary mating elements include, by way of non-limiting example, grooves, threads, etc. Again, a person skilled in the art will appreciate that other fasteners can be used including, for example, hooks, plates, staples, etc.

Figure 3:
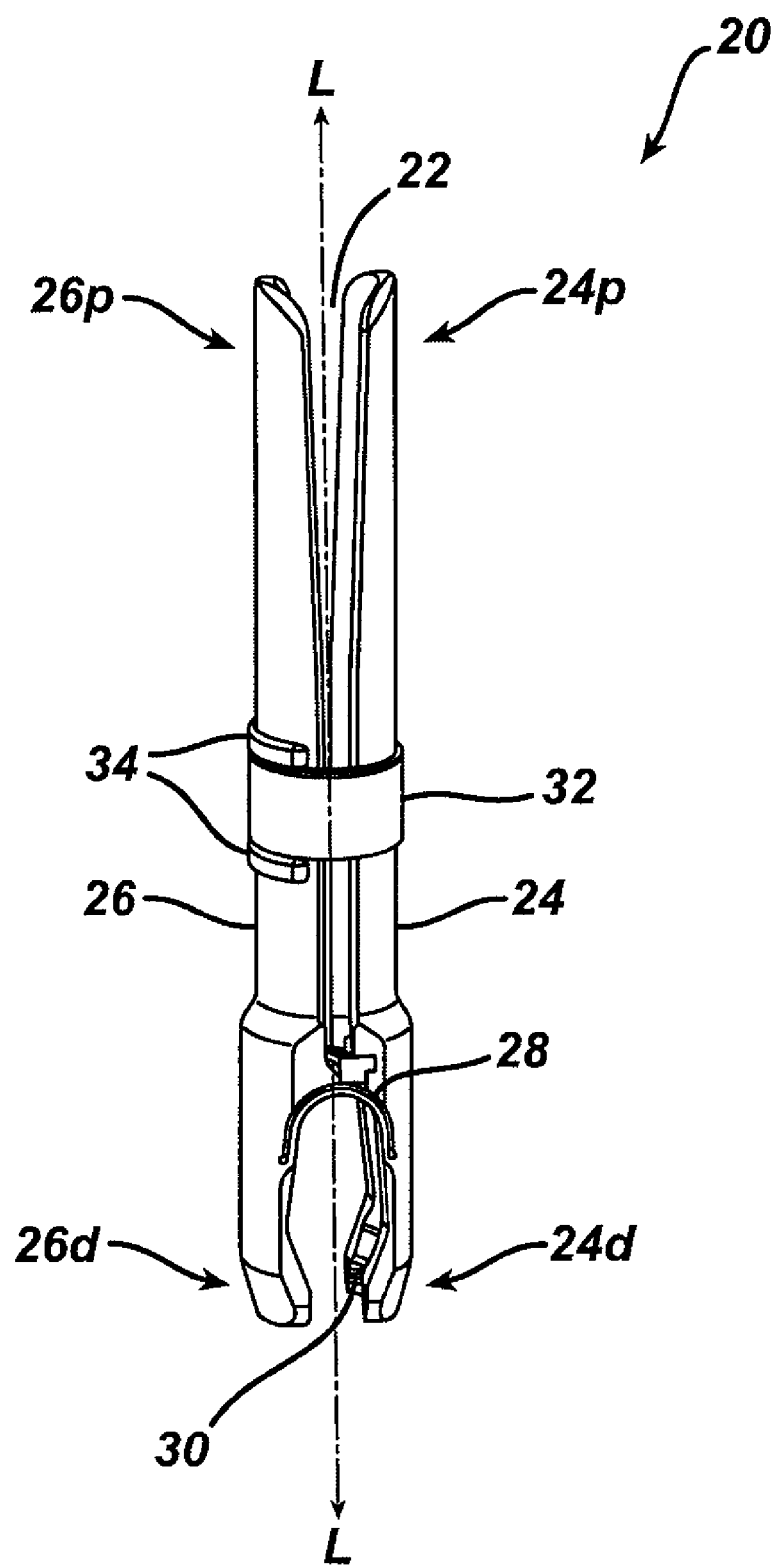
FIG. 3 is a side perspective view of a fastener engaging member of the device of FIG. 1.

The fastener engaging member 20 of the device 10, which is shown in more detail in FIG. 3, can have a variety of configurations but it is preferably adapted to engage at least a portion of a fastener. For example, as shown in FIG. 3, the fastener engaging member 20 can have an elongate substantially cylindrical shape and a pathway 22 extending therethrough. The pathway 22 can serve a number of purposes, but at least two of the advantages provided are that it can be adapted to receive a rod retainer for mating to a fastener engaged by the fastener engaging member 20 and that it can provide access for various instruments to be used in order to communicate with either the rod retainer or the fastener. A person skilled in the art will appreciate that the pathway extending through the fastener engaging member 20 can have any number of sidewall openings and its cross-section does not need to form a complete or continuous closed structure, such as an uninterrupted circle, at any point along the length of the fastener engaging member. A distal end of the fastener engaging member 20 can be adapted to mate to a fastener, such as bone screw 100. In the illustrated embodiment the fastener engaging member 20 includes first and second opposed jaws 24, 26 that extend generally parallel to one another. The jaws 24, 26 can be spaced a distance apart from one another, and they can be movably coupled to one another to allow the jaws 24, 26 to be removably disposed around a portion of a fastener, e.g., around the rod-receiving head 104 of bone screw 100. While various techniques can be used to mate the jaws 24, 26 to the bone screw 100, in the illustrated embodiment the jaws 24, 26 are connected by a u-spring 28.

The u-spring 28 allows the jaws 24, 26 to be flexed apart, e.g., in a radial direction, from a first, relaxed position to facilitate advancement of the jaws 24, 26 longitudinally over the rod-receiving head 104, and when released the u-spring 28 biases the jaws 24, 26 back to an initial position in which the jaws 24, 26 can provide a radially compressive force towards the rod-receiving head 104. In alternative embodiments, the jaws 24, 26 can be connected at a pivot point by a hinge or by other mechanisms for allowing movement between the jaws 24, 26.

Figure 12:
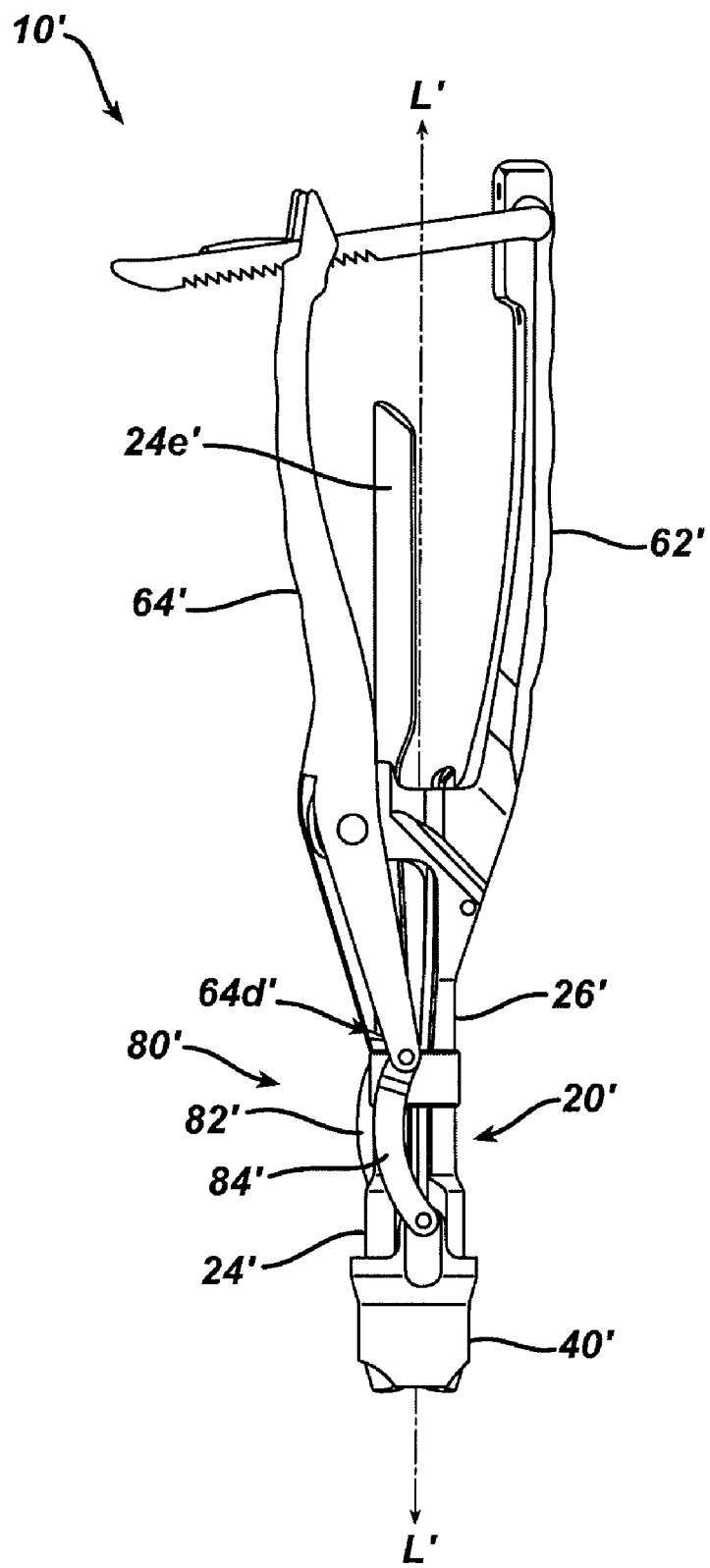
FIG. 12 is a perspective view of yet another embodiment of a spinal rod reduction device.

In another embodiment, as shown in FIG. 12 which illustrates a device 10' that is similar to device 10, at least one of the jaws, e.g., the first jaw 24', can include a proximal extension 24e' that can be used to move the jaws 24', 26' apart to facilitate positioning of the jaws 24', 26' around a fastener. In particular, the first jaw 24' can have a length that is greater than a length of the second jaw 26' such that a proximal end of the first jaw 24' extends proximally beyond a proximal end of the second jaw 26'. This allows the proximal extension 24e' to be grasped and moved toward the second arm 62', thereby moving the distal end of the first jaw 24' away from the distal end of the second jaw 26' to open the jaws 24', 26' for positioning around a fastener. A person skilled in the art will appreciate that a variety of other techniques can also be used to move the jaws to an open position to facilitate positioning around a fastener.

The jaws 24, 26 can also include various features to facilitate mating to a fastener. For example, each jaw 24, 26 can include at least one mating element disposed on an inner surface of a distal end 24d, 26d thereof. By way of a non-limiting example, the mating element can be in the form of at least one projection 30 that extends into at least one detent formed in the rod-receiving head 104, as previously discussed. Exemplary mating techniques are described in more detail in United States Publication No. 2006/0293692 of Whipple et al., filed on Jun. 5, 2005 and entitled "Instruments and Methods for Manipulating a Spinal Fixation Device," U.S. patent application Ser. No. 11/539,496 of Dziedzic et al., filed on Oct. 6, 2006 and entitled "Minimally Invasive Bone Anchor Extension," U.S. Publication No. 2006/0079909 of Runco et al., filed on Sep. 26, 2005 and entitled "Instruments and Methods for Bone Anchor Engagement and Spinal Rod Reduction," and in U.S. Publication No. 2005/0149053 of Varieur et al., filed on Dec. 15, 2003 and entitled "Instruments and Methods for Bone Anchor Engagement and Spinal Rod Reduction," which are hereby incorporated by reference in their entireties. A person skilled in the art will appreciate that the size, shape, and number of mating elements formed on each jaw 24, 26 can vary depending on the configuration of the fastener and the type of connection desired. Still in other embodiments, rather than having jaws 24, 26, the fastener engaging member 20 can include any number of arms, or can have other configurations known in the art for engaging a fastener.

While not necessary, the fastener engaging member 20 can also include a retainer ring 32 disposed around the jaws 24, 26 in order to prevent the jaws 24, 26 from collapsing inwards. In the illustrated embodiment, the retainer ring 32 is disposed around an intermediate portion of the jaws 24, 26 at a location proximal to the u-spring 28. This configuration will prevent a proximal end 24p, 26p of each jaw 24, 26 from moving further apart from one another, thereby preventing the distal ends 24d, 26d of each jaw 24, 26 from collapsing inward. The jaws 24, 26 can also include one or more flanges 34 formed adjacent to one of or both ends of the retainer ring 32 to assist in holding the retainer ring 32 in place.

As previously indicated, the device 10 can also include a reduction member 40 that is movably coupled to the fastener engaging member 20 and that is effective to reduce a spinal fixation element, such as spinal rod 108, into a fastener, such as bone screw 100. The reduction member 40 can be configured in a variety of different ways and with any number of components. In the illustrated embodiment, the reduction member 40 is in the form of a sleeve that is disposed around the jaws 24, 26. A distal end of the reduction member 40 can be configured to abut against a spinal fixation element extending between the opposed jaws 24, 26 of the fastener-engaging member 20, and a proximal end can be coupled to an actuator or handle assembly, as will be discussed in more detail below, for moving the reduction member 40. While not shown, the reduction member 40 can also include features to facilitate engagement with a spinal fixation element. For example, the reduction member 40 can include at least one leg formed on a distal end thereof. The leg(s) can include a recess adapted to receive the spinal fixation element to assist in reducing the spinal fixation element into the fastener. A person skilled in the art will appreciate that any number of legs and/or recesses, or any type of mechanism that is effective to assist with placing a spinal fixation element into a fastener, can be used.

In use, the reduction member 40 can be adapted to slide along the fastener engaging member 20 to allow the reduction member 40 to advance a spinal fixation element into a fastener engaged by the fastener engaging member 20. In an exemplary embodiment, the reduction member 40 can move along a longitudinal axis L of the fastener engaging member 20, as shown in FIG. 3, in order to reduce the spinal rod 108 into the bone screw 100. In particular, the reduction member 40 can be moved between an initial position in which the reduction member 40 is either disengaged with the spinal rod 108 or is placing a negligible force on the rod 108, and a final position in which the reduction member 40 is engaged (i.e., in contact) with the spinal rod 108 and applies a force to the rod 108 to reduce the rod 108 into the bone screw 100. In the initial position, as shown in FIG. 1, the reduction member 40 can be positioned proximal of the distal end 24d, 26d of the jaws 24, 26. In this position, the spinal rod 108 can be disposed between the jaws 24, 26 of the fastener engaging member 20. When the reduction member is slid distally into the final position, as shown in FIG. 2, the reduction member 40 can be positioned adjacent to, i.e., approximately even with or just proximal or distal to, the distal end 24d, 26d of the jaws 24, 26 in order to reduce the rod 108 into the bone screw 100. As further shown in FIG. 2, the reduction member 40 can also be effective to lock the jaws 24, 26 in a fixed position relative to the bone screw 100 when the reduction member 40 is in or near the final position. A person skilled in the art will appreciate that the reduction member 40 can be located in any number of positions and that the initial and final positions can vary depending on the location and configuration of the spinal fixation element and the fastener. Moreover, a person skilled in the art will appreciate that the reduction member does not need to move along the longitudinal axis L of the fastener engaging member 20 in order to perform rod reduction, but rather it can travel in any direction, but preferably in a direction that allows the action of reduction to occur.

In order to move the reduction member 40 between the initial and final positions, the device 10 can further include an actuator or handle assembly 60. The handle assembly 60, which is best illustrated in FIGS. 1 and 2, can have a variety of configurations. In the illustrated embodiment, the handle assembly 60 includes first and second arms 62, 64 that are pivotally coupled to one another. The first arm 62 can have a proximal grasping portion 62p and a distal portion 62d that is mated to the fastener engaging member 20, and the second arm 64 can have a proximal grasping portion 64p and a distal portion 64d that is coupled to a linkage 80 such that movement of the second arm 64 relative to the first arm 62 causes the reduction member 40 to move relative to the fastener engaging member 20. The shape of each arm 62, 64 can vary, but in an exemplary embodiment the first arm 62 is substantially L-shaped such that the proximal portion 62p of the first arm 62 extends substantially parallel to the longitudinal axis L of the fastener engaging member 20 and the distal portion 62d of the first arm 62 extends substantially transverse to the proximal portion 62p of the first arm 62. The first arm can be fixedly or movably mated to the fastener engaging member 20 at a variety of locations. In an exemplary embodiment, the distal portion 62d of the first arm 62 is fixedly mated to the proximal end 24p of the first jaw 24. As shown, the distal portion 62d of the first arm 62 can include a forked extension 66 that receives the proximal end 24p of the first jaw 24. As further shown in FIGS. 1 and 2, the second arm 64 can have a generally elongate substantially linear shape, and it can be pivotally coupled to the first arm 62, e.g., using a pin or similar mating element. While the pivot location can vary, in the illustrated embodiment the pivot 70 is located at a mid-portion of the second arm 64 and on the distal portion 62d of the first arm 62. The second arm 64 can include a forked extension 68 formed in the distal portion 64d thereof for receiving the distal end 62d of the first arm 62 therebetween. The illustrated forked extension 68 of the second arm 64 begins at a mid-portion and extends distally. The arms 62, 64 can also optionally include features that assist in the comfort and ease of use of the device 10. Any number of features can be included to provide such comfort and ease of use. For example, the arms 62, 64 can include surface features to facilitate engagement, such as finger grips, which are represented in the FIGS. by contours or depressions 67 formed in the respective proximal portions 62p, 64p of the arms 62, 64.

Actuation of the handle assembly 60 can be achieved by moving one of the grasping proximal portions 62p, 64p of the first and second arms 62, 64 toward the other one of the grasping proximal portions 62p, 64p of the first and second arms 62, 64, or alternatively, by moving both of the grasping proximal portions 62p, 64p toward each other. In the illustrated embodiment, the second arm 64 functions as an actuator that can be moved toward the first arm 62. Such movement causes the distal portion 64d of the second arm 64 to move toward the longitudinal axis L of the fastener engaging member 20 such that the distal portion 64d of the second arm 64 extends substantially parallel to both the fastener engaging member 20 and the grasping proximal portion 62p of the first arm 62. The distal portion 64d of the second arm 64 can also crossover beyond the longitudinal axis of the fastener engaging member 20 and the grasping proximal portion 62p of the first arm 62.

Figure 4:
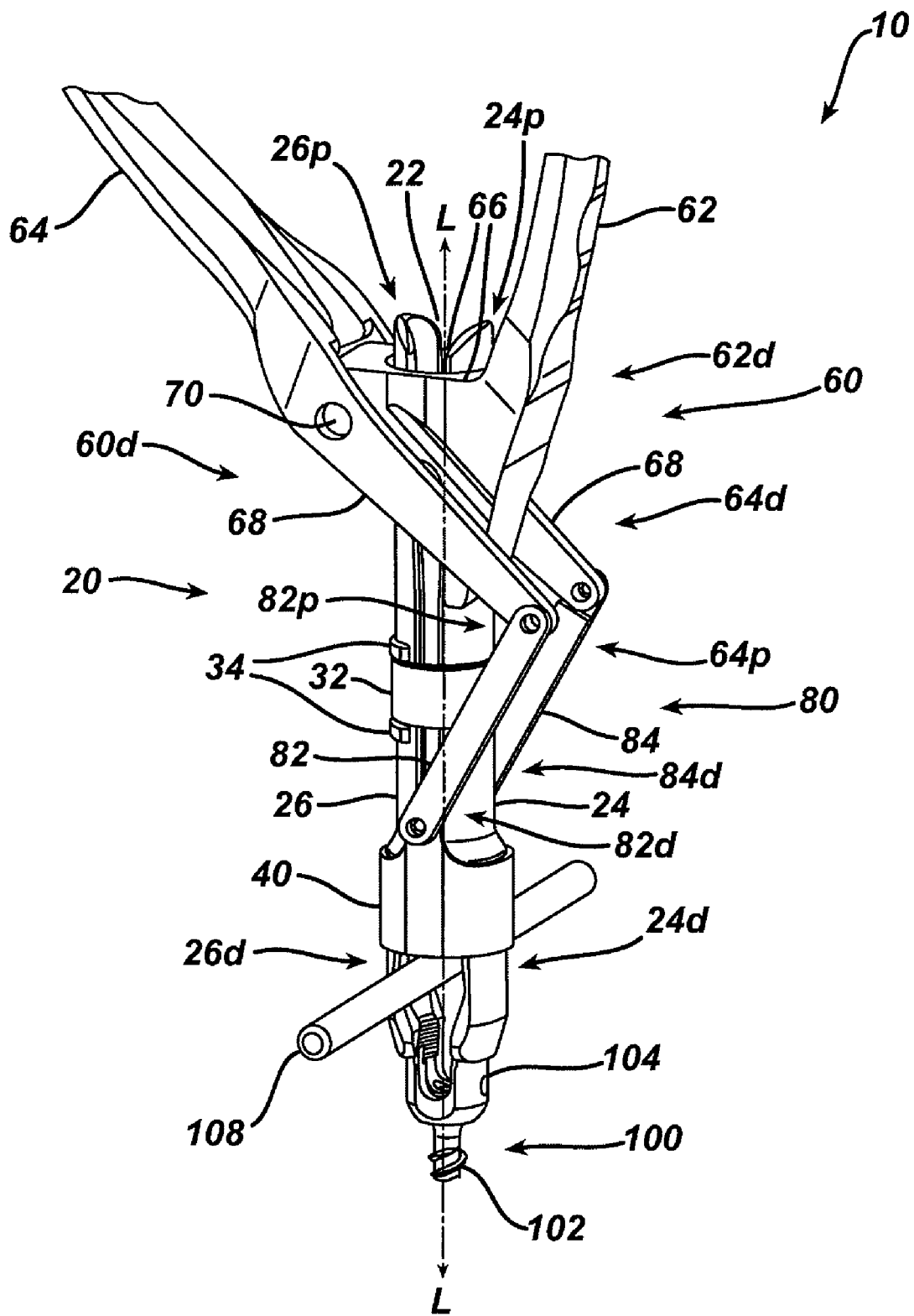
FIG. 4 is a partial enlarged side perspective view of the device of FIG. 1, illustrating a fastener engaging member, a reduction member, and a linkage.

In order for movement of the arms 62, 64 to be effective to move the reduction member 40, the device 10 can also include a linkage 80, or other similar mechanism known in the art, coupled between the second arm 64 and the reduction member 40. The linkage 80, which is shown in more detail in FIG. 4, can have a variety of configurations. In the illustrated embodiment, the linkage 80 includes first and second bars 82, 84 positioned on opposed sides of the fastener engaging member 20. Each bar 82, 84 can include a proximal end 82p, 84p and a distal end 82d, 84d, respectively. The proximal ends 82p, 84p of the first and second bars 82, 84 can be pivotally mated to the distal portion 64d of the second arm 64, i.e., to the terminal ends of the forked extension 68, and the distal ends 82d, 84d of the first and second bars 82, 84 can be mated to the reduction member 40. A person skilled in the art will recognize that any number of methods for mating the linkage 80 to the second arm 64 and the reduction member 40 can be used, including, for example, a pin. In use, the linkage 80 can extend between an initial position in which the linkage extends substantially transverse to the longitudinal axis L of the fastener engaging member 20, as shown in FIG. 1, and a final position in which the linkage 80 extends substantially parallel to the longitudinal axis L of the fastener engaging member 20, as shown in FIG. 2. In particular, as described above with respect to the arms 62, 64, movement of the proximal grasping portion 64p of the second arm 64 toward the proximal grasping portion 62p of the first arm 62 will cause the distal portion 64d of the second arm 64 to move toward the longitudinal axis L. The distal portion 64d will thus move the proximal ends 82p, 84p of the first and second bars 82, 84 toward the longitudinal axis L of the fastener engaging member 20. Because the distal ends 82d, 84d of the first and second bars 82, 84 are mated to the reduction member 40, the reduction member 40 is subsequently moved toward the distal end 24d, 26d of the jaws 24, 26 as the linkage 80 moves toward the final position. As a result, the fastener engaging member 20 can reduce the rod 108 into the bone screw 100.

A person skilled in the art will appreciate that, while the device 10 of FIG. 1 includes a linkage 80 having two bars 82, 84 that are straight, the linkage can have a variety of other configurations. FIG. 12 illustrates another embodiment of a spinal rod reduction device 10' that is similar to device 10, except that the linkage 80' has two bars 82', 84' that each have a curved shaped. In use, the linkage 80' functions similar to the linkage 80 of FIG. 1. Namely, the linkage 80' can extend between an initial position in which the bars 82', 84' extend substantially transverse to a longitudinal axis L' of the fastener engaging member 20', and a final position in which the bars 82', 84' extend substantially parallel to the longitudinal axis L' of the fastener engaging member 20', as shown in FIG. 12. While the bars 82', 84' are curved, at least the proximal and distal pivots points at which the bars 82', 84' pivotally mate to the distal portion 64d' of the second arm 64' and the reduction member 40' can be aligned with the longitudinal axis L'.

Exemplary methods for reducing a spinal fixation element, such as a spinal rod 108, into a fastener, such as a bone screw 100, are also provided. In one embodiment, one or more bone screws 100 can be implanted in one or more vertebra using known surgical techniques and the spinal rod 108 can be positioned to span across the bone screw(s) 100. Since multiple bone screw implanted in adjacent vertebrae are not always aligned with one another, the spinal rod 108 may be positioned a distance above one or more of the bone screws 100, and thus reduction of the rod 108 into the screws(s) 100 is necessary. Accordingly, a fastener engagement member 20 can be engaged with a bone screw 100. In particular, the proximal ends 24p, 26p of the jaws 24, 26 can be squeezed together to move the distal ends 24d, 26d of the jaws 24, 26 apart, thereby allowing the jaws 24, 26 to be positioned around the rod-receiving head 104 of the bone screw 100. Once the jaws 24, 26 are positioned around the rod-receiving head 104 of the bone screw 100, the proximal ends 24p, 26p of the jaws 24, 26 can be released to allow the mating elements on the fastener engaging member 20 to engage the detents in the bone screw 100.

Once the fastener engaging member 20 is engaged with at least a portion of the bone screw 100, the handle assembly can be operated in order to reduce the rod 108 into the bone screw 100. In particular, as discussed above, the second arm 64 of the device 10 can be pivoted relative to the first arm 62 to cause the proximal portion 64p of the second arm 64 to move toward the proximal portion 62p of the first arm 62. Movement of the second arm 64 will in turn cause the linkage 80 to move distally, thereby advancing the reduction member 40 distally toward the bone screw 100 into its final position. As a result, the spinal rod 108 will be advanced into the rod-receiving head 104 of the bone screw 100. The reduction member 40 also lock the jaws 24, 26 in a fixed position relative to the bone screw 100 as it will extend around the jaws 24, 26 to prevent them from opening. Locking can occur prior to the full reduction of the spinal rod 108 into the bone screw 100, or it can occur simultaneously.

Figure 5:
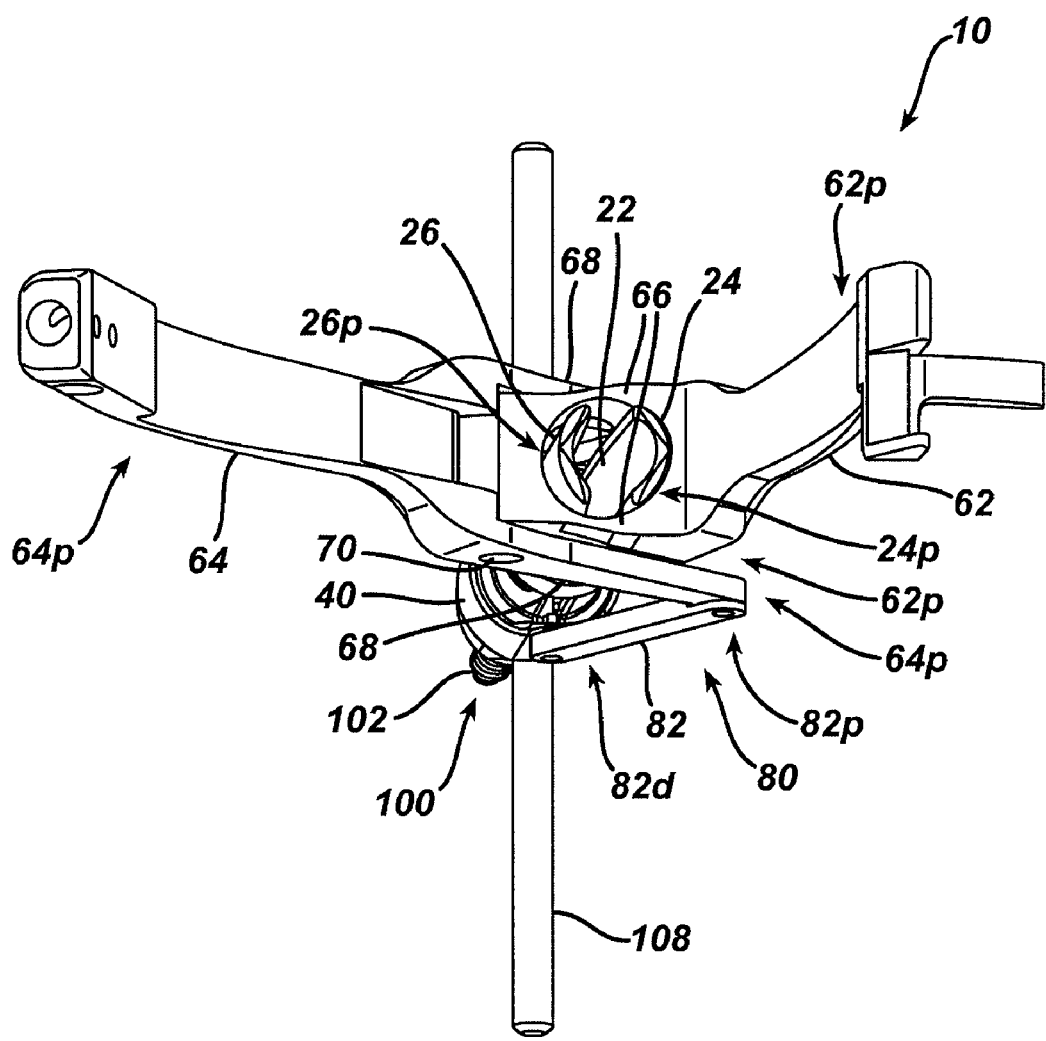
FIG. 5 is a top perspective view of the device of FIG. 1.

Once the final position has been reached and the spinal rod 108 has been reduced into the bone screw 100, a rod retainer, such as a set screw, can be delivered to the bone screw 100 to lock the rod 108 into the screw 100. In an exemplary embodiment, the rod retainer is delivered through the pathway 22 extending through the fastener engaging member 20. The pathway, as seen in FIG. 5, can be a linear pathway extending between the arms 62, 64 and extending through the fastener engaging member 20. This linear pathway can provide an easy viewing area for performing the reduction and subsequently delivering the rod retainer. Once the rod retainer is delivered to the bone screw 100, it can be applied to the bone screw 100 using various techniques, such as threads or a twist-lock connection. An instrument, such as a driver, can be placed within the pathway 22 to assist in delivering and applying the rod retainer to the bone screw 100.

In another embodiment, the first arm 62 can be removable to allow a fastener engaging member 20 to be mated to a bone screw 100 before attaching the first arm 62 to the fastener engaging member 20. This can be advantageous where multiple bone screws are disposed in adjacent vertebrae and multiple fastener engaging members are engaged with each bone screw prior to performing any reductions. Once the fastener engaging members are in place, a single arm can be sequentially mated to each fastener engaging member to reduce the spinal rod into the bone screws.

Figure 6:
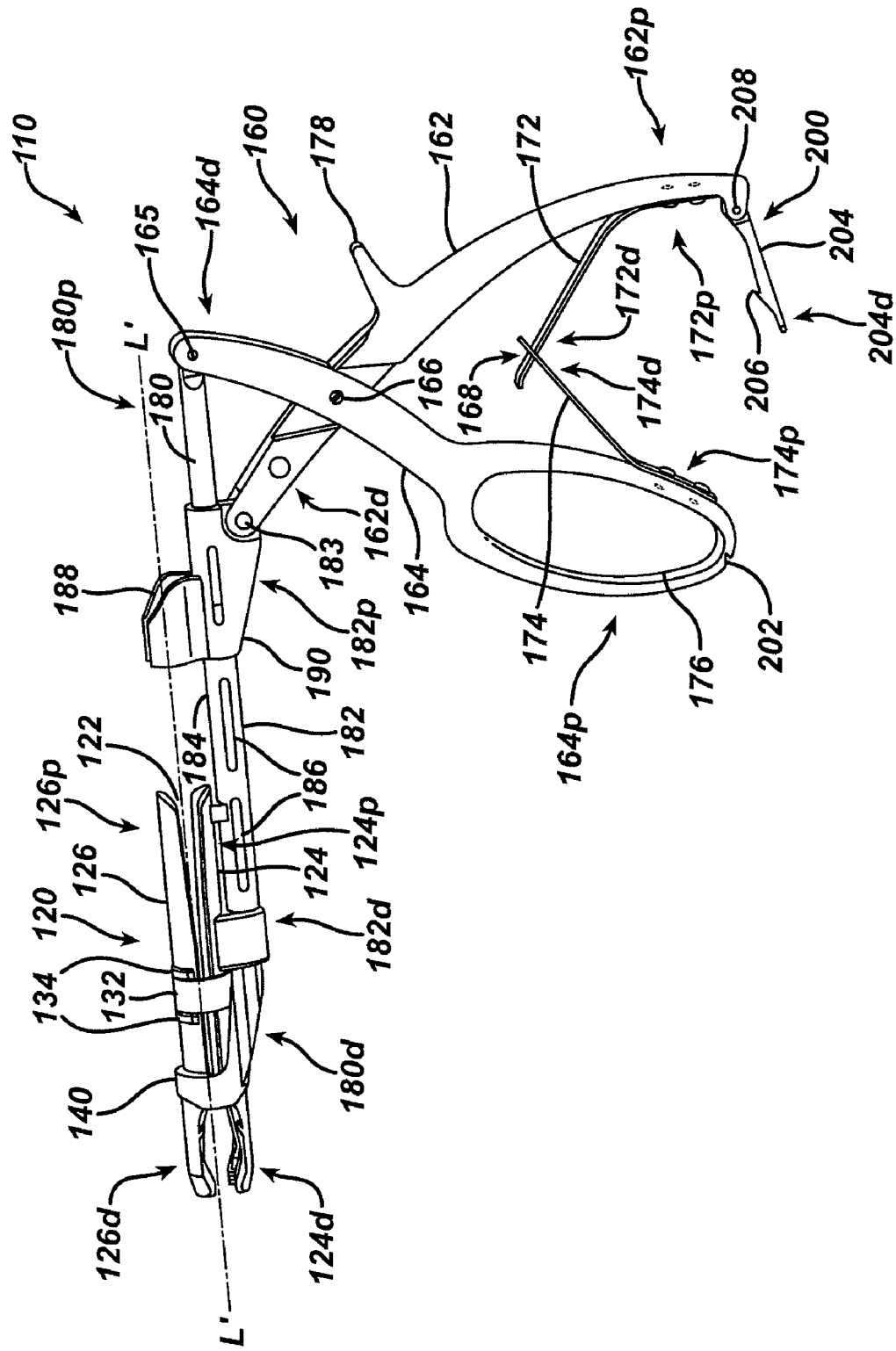
FIG. 6 is a side perspective view of another exemplary embodiment of a spinal rod reduction device in an initial position.
Figure 7:
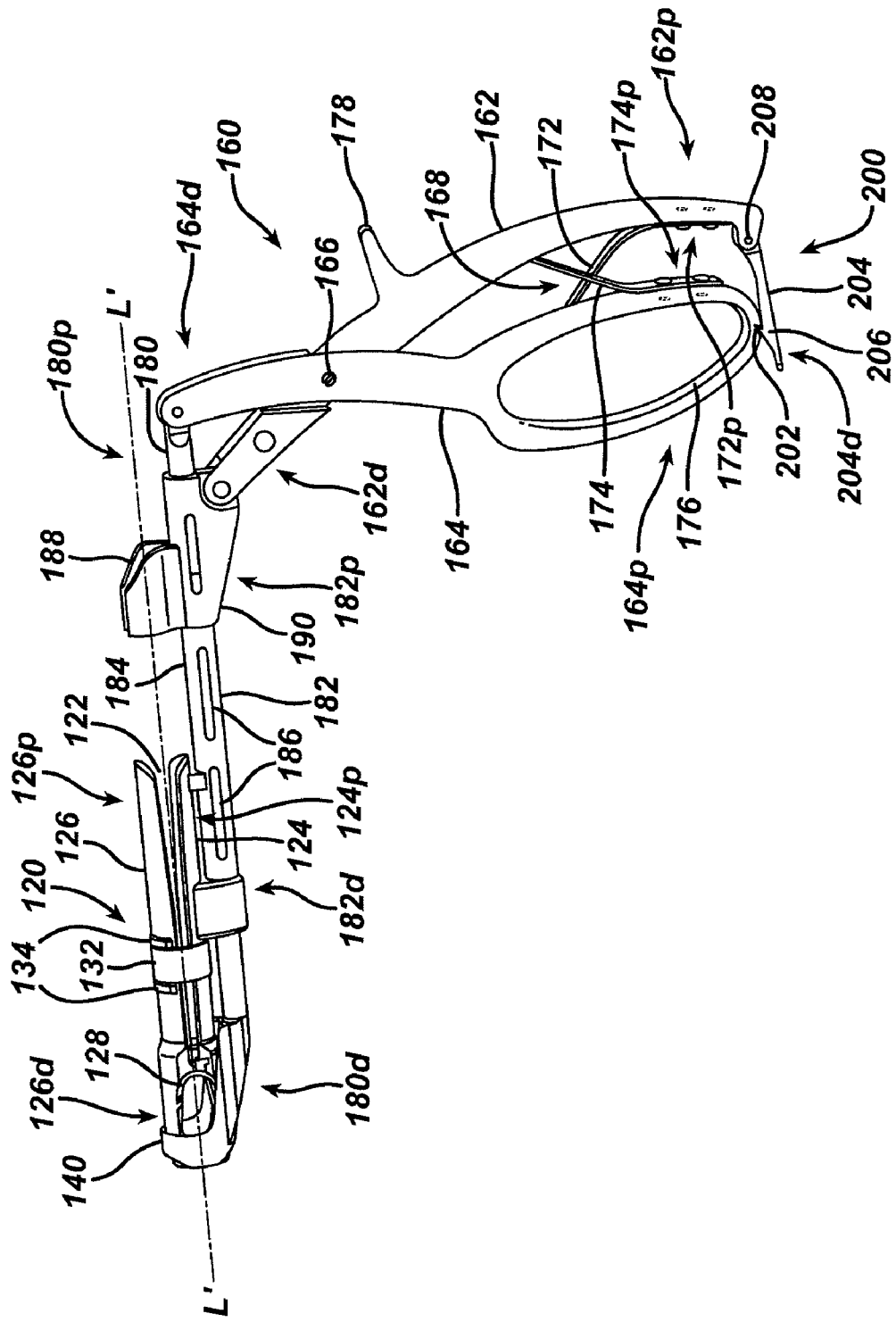
FIG. 7 is a side perspective view of the device of FIG. 6 in a final position.

FIGS. 6 and 7 illustrate another exemplary embodiment of a spinal rod reduction device 110. The device 110 is similar to device 10 in that it generally includes a fastener engaging member 120 adapted to engage at least a portion of a fastener, a reduction member 140 movably coupled to the fastener engaging member 20, and a handle assembly 160 mated to the reduction member 140 and adapted to move the reduction member 140 relative to the fastener engaging member 120 to reduce a spinal fixation element into a fastener. In this embodiment, rather than having a linkage, the device 110 includes a pusher member 180 that can both extend through a housing 182 mated to the fastener engaging member 120 and also can be mated to the reduction member 140. The handle assembly 160 is configured to advance the pusher member 180 distally which in turn is effective to move the reduction member 140 and reduce the spinal fixation element into the fastener.

The illustrated fastener engaging member 120 is similar to fastener engaging member 20 and it generally includes first and second opposed jaws 124, 126 with proximal ends 124p, 126p and distal ends 124d, 126d, respectively, and a pathway 122. Similar to device 10, various techniques and features can be used to mate the jaws 124, 126 to allow movement between the jaws 124, 126, such as a u-spring 128, and also similar to device 10, the jaws 124, 126 can be flexed apart, e.g., in the radial direction, from a first, relaxed position to facilitate advancement of the jaws 124, 126 longitudinally over the rod-receiving head 104 of the bone screw 100 back to an initial position in which the jaws 124, 126 can provide a radially compressive force on the rod-receiving head 104. Furthermore, as previously described with respect to device 10, the fastener engaging member 120 can also include various mating elements to engage a fastener and/or a retainer ring 132 to prevent the jaws 124, 126 from collapsing inwards.

As previously indicated, the device 110 can also include a reduction member 140 that is movably coupled to the fastener engaging member 120 and that is effective to reduce a spinal fixation element, such as spinal rod 108, into a fastener, such as bone screw 100. The illustrated reduction member 140 is similar to the reduction member 40 previously described for device 10 and is generally in the form of a sleeve disposed around the fastener engaging member 120. In use, the reduction member 140 can move along a longitudinal axis L' of the fastener engaging member 120 between an initial position and a final position as described above with respect to device 10 to allow the reduction member 140 to advance a spinal fixation element into a fastener engaged by the fastener engaging member 120. Also similar to the device 10, the reduction member 140 can be effective to lock the jaws 124, 126 in a fixed position relative to the bone screw 100 when the reduction member 140 is moved toward or into the final position.

In order to move the reduction member between the initial and final positions, the device 110 can further include a pusher member 180, such as a rod. A distal end 180d of the pusher member 180 can abut against the rod reduction member 140, but in an exemplary embodiment the distal end 180d is fixedly mated to or formed integrally with the rod reduction member 140. As shown in FIG. 6, the rod reduction member 140 is formed on the distal end 180d of the pusher member 180. The pusher member 180 can also extend offset from but substantially parallel to a longitudinal axis L' of the fastener engaging member 120, and thus the distal end 180d of the pusher member 180 can extend at an angle relative to an axis of the remainder of the pusher member 180 and toward longitudinal axis L' of the fastener engaging member 120 to allow the pusher member 180 to mate to the reduction member 140.

As further shown in FIG. 6, at least a portion of the pusher member 180 can be slidably disposed within a housing 182. In one embodiment, the housing 182 is a hollow elongate cylindrical member with a proximal portion 182p and a distal portion 182d. The housing 182 can include an outer sidewall 184, which can optionally include one or more openings 186 formed therein for facilitating viewing and/or cleaning of the device 110. The outer sidewall 184 of the housing 182 can be mated to the fastener engaging member 120 to allow the pusher member 180 to apply a force to the reduction member 140 while the housing maintains the fastener engaging member 120 in a fixed position. As shown in FIG. 6, an intermediate portion of the housing 182 is fixedly mated to the proximal end 124p of the first jaw 124, and the distal portion of the housing 182d is fixedly mated to an intermediate portion of the fastener engaging member 120. As a result, the housing 182, as well as the pusher member 180 extending through the housing 182, is offset from but substantially parallel to the longitudinal axis L' of the fastener engaging member 120. A person skilled in the art will appreciate that any number of connections and methods to make such connections between the housing 182 and the fastener engaging member 120 can be used.

As further shown in FIG. 6, the housing 182 can also include an alignment extension 188 that can be aligned with the pathway 122 of the fastener engaging member 120 to assist in aligning various devices with the fastener engaging member 120. The alignment extension 188 can have any configuration, but in the illustrated embodiment it is substantially c-shaped for receiving an instrument, such as a screwdriver, therethrough and for aligning the instrument with the pathway 122. The alignment extension 188 can be located anywhere on the housing 182, but in the illustrated embodiment it is located on the proximal portion 182p of the housing 182.

In use, the pusher member 180 can be slidably advanced through the housing 182 to cause distal movement of the reduction member 140 along the fastener engaging member 120 to thereby reduce the spinal rod 108 into the bone screw 100. In particular, the pusher member 180 can travel substantially parallel to the longitudinal axis L' of the fastener engaging member 120 from an initial position, shown in FIG. 6, in which a distal-most end of the pusher member 180, and thus the reduction member 140, is proximal or adjacent to the u-spring 128 between the jaws 124, 126 to allow the jaws 124, 126 to flex open and engage a bone screw, to a final position in which the distal-most end of the pusher member 180, and thus the reduction member 140, is adjacent to the distal ends 124d, 126d of the jaws 124, 126, as shown in FIG. 7. to thereby reduce a rod into a bone screw.

In order to move the pusher member 180 between the initial and final positions, the device 110 can further include a handle assembly 160. The handle assembly 160, which is best illustrated in FIGS. 6 and 7, can have a variety of configurations. In the illustrated embodiment, the handle assembly 160 includes first and second arms, hereinafter referred to as a handle 162 and an actuator 164, that are pivotally coupled to one another. The handle 162 can have a proximal grasping portion 162p and a distal portion 162d that is coupled to the proximal end 182p of the housing 182 at a pivot point 183. The housing 182 can optionally include a flared portion 190 that allows for easy mating between the housing 182 and the handle 162. The handle 162 can also be integrally formed with the housing 182. The actuator 164 can also include a proximal grasping portion 164p and a distal portion 164d that is coupled to the proximal end 180p of the pusher 180 at a pivot point 165. As indicated above, the handle 162 and the actuator 164 can be pivotally mated to one another. While the pivot location can vary, in the illustrated embodiment a pivot 166 is located at mid-portions of the handle 162 and the actuator 164. The pivot 166 can be in the form of a pin extending through the handle 162 and the actuator 164, although a person skilled in the art will appreciate that any known component capable of allowing pivotable movement between the handle 162 and the actuator 164 can be used.

The handle assembly can also include a biasing element 168 adapted to bias at least one of the handle 162 and the actuator 164 in one of an open or a closed position. The biasing element 168 can be disposed between the handle 162 and the actuator 164, or it can be located in any other location that allows for one of the handle 162 and the actuator 164 to be biased to at least one of the open or closed positions. In the illustrated embodiment, the biasing element 168 is two leaf springs, with the first leaf spring 172 mated at a proximal end 172p thereof to an inner surface of the proximal grasping portion 162p of the handle 162 and the second leaf spring 174 mated at a proximal end 174p thereof to an inner surface of the proximal grasping portion 164p of the actuator 164. The first and second leaf springs 172, 174 can be connected at distal ends 172d, 174d thereof. As a result, the biasing mechanism 168 will maintain the handle assembly in the open position, as shown in FIG. 6, and a force sufficient to overcome the biasing force will need to be applied to the handle assembly 160 to move it toward the closed position, which is shown in FIG. 7.

The handle 162 and the actuator 164 can also optionally include features that assist in the comfort and ease of use of the device 110. Any number of features can be included to provide such comfort and ease of use. For example, the proximal grasping portion 164p of the actuator 164 can include a loop 176 which provides an area for fingers to be placed during use of the device 110, and the proximal grasping portion 162p of the handle 162 can include a thumb stop 178, which provides an area for the thumb to be placed during use of the device 110.

The handle assembly 160 can be actuated by moving one of the grasping proximal portions 162p, 164p of the handle 162 and the actuator 164, respectively, toward the other one of the proximal portions 162p, 164p of the handle 162 and the actuator 164, or alternatively, by moving both of the grasping proximal portions 162p, 164p toward each other. In the illustrated embodiment, the handle 162 is pivotally connected to the housing 182 at the pivot point 183 and thus can pivot as the actuator 164 pivots about pivot point 166 toward the handle 162. Such movement can cause the distal end 164d of the actuator 164 to move toward the distal end 162d of the handle 162 thereby causing the pusher member 180 to advance distally toward the reduction member 140 to reduce the spinal rod 108 into the bone screw 100. Alternatively, the handle 162 can be fixed to the housing 182 at point 183 while the actuator 164 is movably coupled to the proximal portion of the pusher 180 at pivot point 165. In other words handle 162 shown in FIGS. 6 and 7 can form a fixed handle while actuator 164 shown in FIGS. 6 and 7 remains movably coupled to the pusher. Such a configuration will likewise result in movement of the pusher 180 relative to the reduction member 140 to reduce a spinal rod 108 into a bone screw 100.

Exemplary methods for reducing a spinal fixation element into a fastener using device 110 are also provided. As previously discussed, a bone screw 100 can be implanted in a vertebra using known surgical techniques and the fastener engaging member 120 can be mated to the bone screw 100. The fastener engaging member 120 can be positioned around a spinal rod 108, positioned above the bone screw 100, such that the rod 108 extends between the jaws 124, 126 of the fastener engaging member 120. Once the fastener engaging member 120 is mated to the bone screw 100, the pusher member 180 can be moved through the housing 182 toward the bone screw 100 to advance the reduction member 140 toward the bone screw 100. In particular, the proximal grasping portion 164p of the actuator 164 can be pivoted toward the proximal grasping portion 162p of the handle 162 to cause the pusher member 180 to move distally, thereby advancing the reduction member 140 distally toward the bone screw 100 into its final position. As a result, the spinal rod 108 will be advanced into the rod-receiving head 104 of the bone screw 100. The reduction member 140 can also lock the jaws 124, 126 in a fixed position relative to the bone screw 100. Locking can occur prior to the full reduction of the spinal rod 108 into the bone screw 100, or it can occur simultaneously. Once the final position has been reached and the spinal rod 108 has been reduced into the bone screw 100, a rod retainer, such as a set screw, can be delivered to the bone screw 100. An instrument such as a driver can be positioned through the alignment extension 188 and the pathway 122 to deliver and apply the rod retainer to the bone screw 100.

The various devices discussed herein, as well as other devices known in the art, can also include a locking mechanism that is adapted to maintain the reduction member in a desired fixed position. The desired fixed position can be any position between and including the initial and final positions as described above. FIGS. 6 and 7 illustrate one exemplary embodiment of a locking mechanism 200 for locking the reduction member 140 in a fixed position relative to the fastener engaging member 120. As shown, locking mechanism 200 is in the form of a catch bar 204 that is coupled to the proximal grasping portion 162p of the handle 162 and that is adapted to engage a notch 202 formed in a proximal grasping portion 164p of the actuator 164. The catch bar 204 can be generally elongate, and on one end it can be pivotally mated to the proximal grasping portion 162p of the handle 162 at a pivot point 208. This pivotal connection allows the catch bar 204 to move between various positions, as will be discussed below. The other end of the catch bar 204 can include a latch 206 that is configured to engage the notch 202.

In use, the catch bar 204 can be moved between an engaged and a disengaged position by engaging and disengaging the latch 206 from the notch 202. When the catch bar 204 is in the engaged position, as shown in FIG. 7, the handle 162 and the actuator 164 are maintained in a fixed position relative to one another, which in turn means that the pusher member 180 and the reduction member 140 coupled thereto are also maintained in a fixed position because of the communication between the pusher member 180 and the handle assembly 160. When the catch bar 204 is in the disengaged position, as shown in FIG. 6, the handle 162 and/or the actuator 164 can move freely, which in turn means that the pusher member 180 and the reduction member 140 coupled thereto can also move freely. In the illustrated embodiment, the catch bar 204 is pivotally mated to the proximal grasping portion 162p of the handle 162 at the pivot point 208, and thus the catch bar 204 can be located in a variety of places when it is in the disengaged position. For example, the catch bar 204 can be substantially parallel to the handle 162 with a distal end 204d of the catch bar being directed either toward the device 110 or away from the device 110. By way of another example, the catch bar 204 can be substantially transverse to the handle 162 with the distal end 204d of the catch bar 204 being directed proximally away from the device 110. The catch bar 204 can be rotated or snapped into the variety of disengaged positions.

Figure 8:
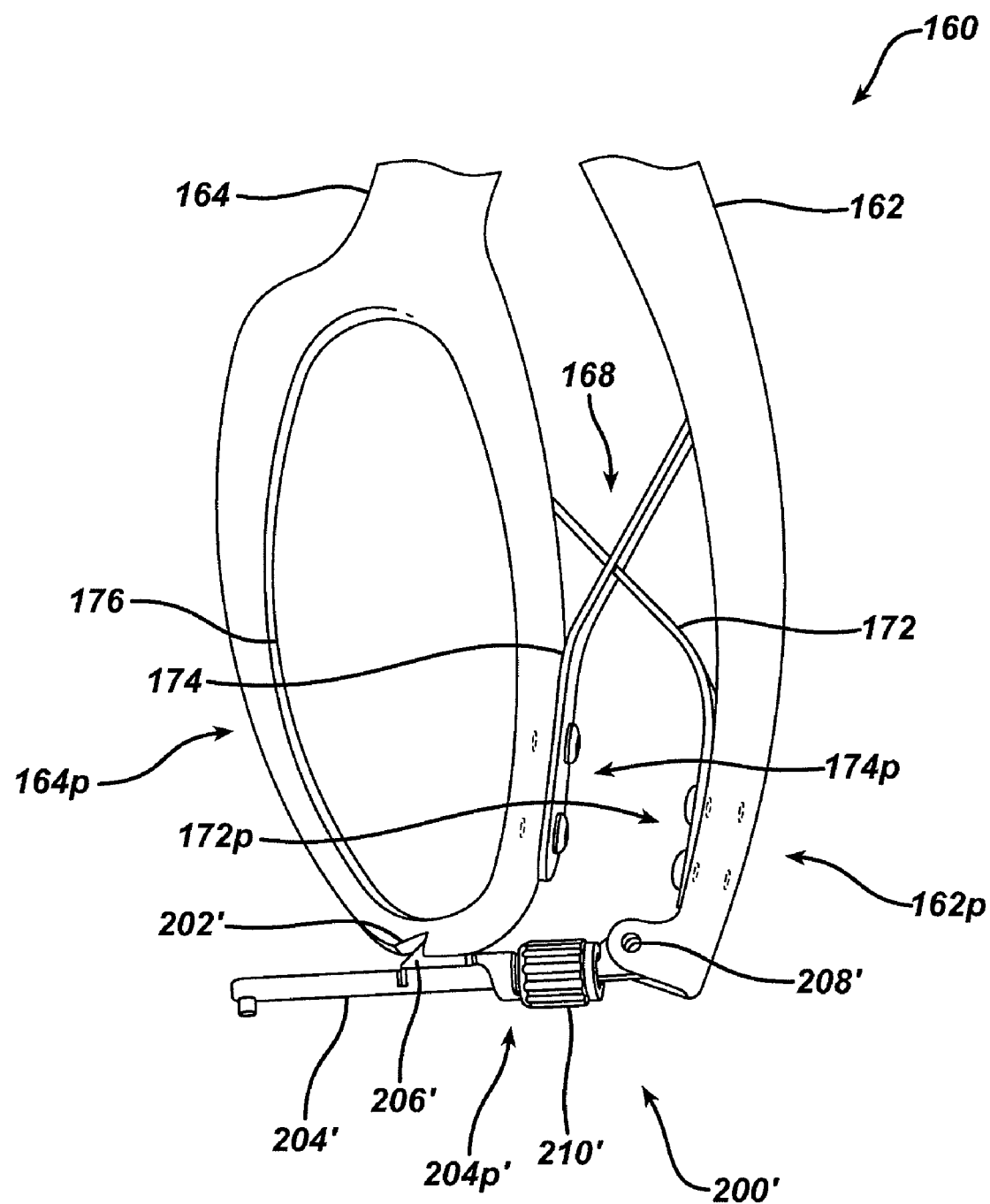
FIG. 8 is a partial side perspective view of one embodiment of a locking mechanism for use with a spinal rod reduction device.

FIG. 8 illustrates another embodiment of a locking mechanism 200' having a catch bar 204' that includes a threaded collar 210' rotatably (or threadably) coupled to the catch bar 204' and that is adapted to adjust an effective length of the catch bar 204' to allow the locking mechanism 200' to maintain the reduction member 140 in a number of different positions. More particularly, rotation of the threaded collar 210' can allow the latch 206' to move toward and away from a pivot point 208', thereby adjusting the effective length of the catch bar 204'. As a result, the catch bar 204' will maintain the handle 162 and the actuator 164 at a desired, operator-selected distance apart, which in turn maintains the pusher member 180 and the reduction member 140 coupled thereto in a desired, operator-selected position because of the communication between the pusher member 180 and the handle assembly 160. Similarly, the threaded collar 210' could be rotatably coupled to the handle portion 162p, while the catch bar 204' with latch 206' can be moved toward and away from a pivot point 208' by rotation of threaded collar 210'.

Figure 9:
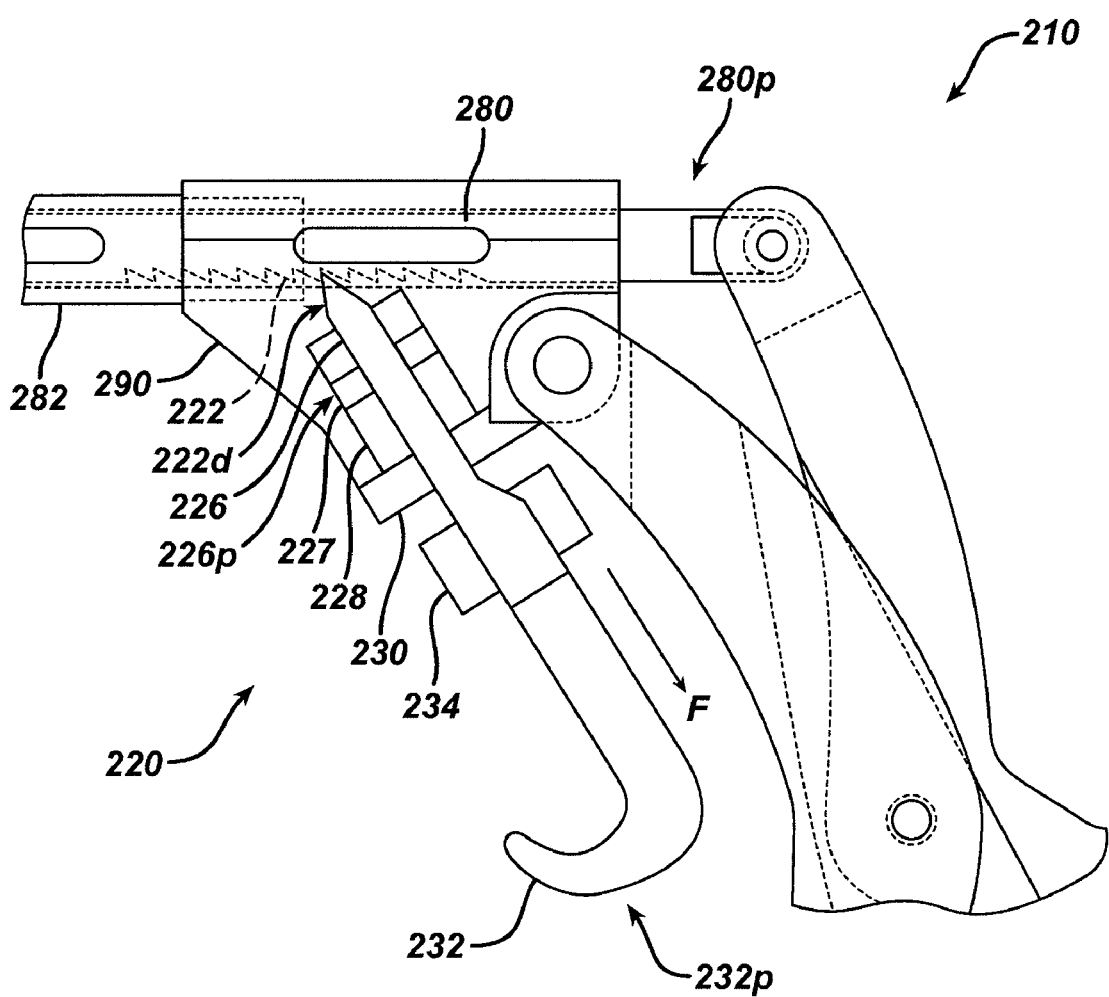
FIG. 9 is a partially transparent side view of another embodiment of a locking mechanism for use with a spinal rod reduction device.

FIG. 9 illustrates another embodiment of a locking mechanism 220. In this embodiment, the locking mechanism 220 includes a locking pin 226 coupled to a housing 282, as well as a series of notches 222 formed in a proximal end 280p of a pusher member 280 of a device 210 having a configuration similar to device 110 of FIGS. 6 and 7. The locking pin 226 can have a generally elongate shape with a proximal end 226p positioned outside of the housing 282 formed on the handle of the device 210, and a distal end 226d disposed within the housing 282 and adapted to selectively engage the series of notches 222. The locking pin 226 can be movable between an engaged position, shown in FIG. 9, in which the distal end 226d is in contact with the notches 222, and a disengaged position, in which the distal end 226d is spaced a distance apart from the pusher member 280. A person skilled in the art will appreciate that, while a series of notches 222 is shown, the pusher member 280 can include a single notch.

In an exemplary embodiment, the locking pin 226 can be biased to the engaged position. As shown in FIG. 9, the device includes a spring 228 disposed within the housing 282 and around the locking pin 226. The spring can extend between a flange 227 formed adjacent to the distal end 226d of the locking pin 226 and a portion of the housing 282 through which the pin 226 extends. As a result, the spring 228 applies a force to the flange 227, thereby biasing the pin 226 toward and into engagement with the notches 222. FIG. 9 illustrates a nut or screw 230 disposed within the housing 282 and having the locking pin 226 extending through a bore formed therein. The screw 230 can be provided for allowing insertion of the spring 228 into the housing 282 during manufacturing of the device. A person skill in the art will appreciate that the spring 228 can alternatively bias the locking pin 226 into a disengaged position, in which the locking pin 226 is spaced apart from the series of notches 222 in the pusher member 280, and thus the pusher member 280 and the reduction member coupled thereto can move freely.

The locking mechanism 220 can also include a release 232 coupled to the proximal end 226p of the locking pin 226 to unbias the locking pin 226 and place the locking pin 226 in the disengaged position. In the illustrated embodiment, the release 232 is in the form of a handle extending from or formed integrally with the proximal end 226p of the locking pin 226. As shown, a proximal end 232p of the release 232 can be curved to allow a finger to grasp the release 232. In use, movement of the release 232 in a direction indicated by arrow F will pull the locking pin 226 out of engagement with the notches 222, thereby allowing free movement of the pusher member 280 and the reduction member coupled thereto. A person skilled in the art will appreciate that the release can have a variety of other configurations and it can be coupled to any component of the device, including the screw 230, the spring 228, or the locking pin 226, to selectively move the locking pin 226 between the engaged and disengaged positions.

As further shown in FIG. 9, the locking mechanism 220 can also include a blocking mechanism adapted to prevent the locking pin 226 from engaging the series of notches 222. In the illustrated embodiment, the blocking mechanism is a nut 234 that is threadably disposed around the proximal end 226p of the locking pin 226 and that is located outside of the housing 282. In use, the nut 234 can be rotated relative to the locking pin 226 to pull the locking pin 226 away from the notches 222. Since the nut 234 abuts against the housing, and in particular against the screw 230, the nut 234 will maintain the locking pin 226 in the disengaged positions. Threading the nut 234 in the opposite direction can place the locking pin 226 back into the engaged position. A person skilled in the art will appreciate that there are a number of different ways to design the blocking mechanism so that it selectively places the locking pin 226 in the engaged and disengaged positions.

Figure 10:
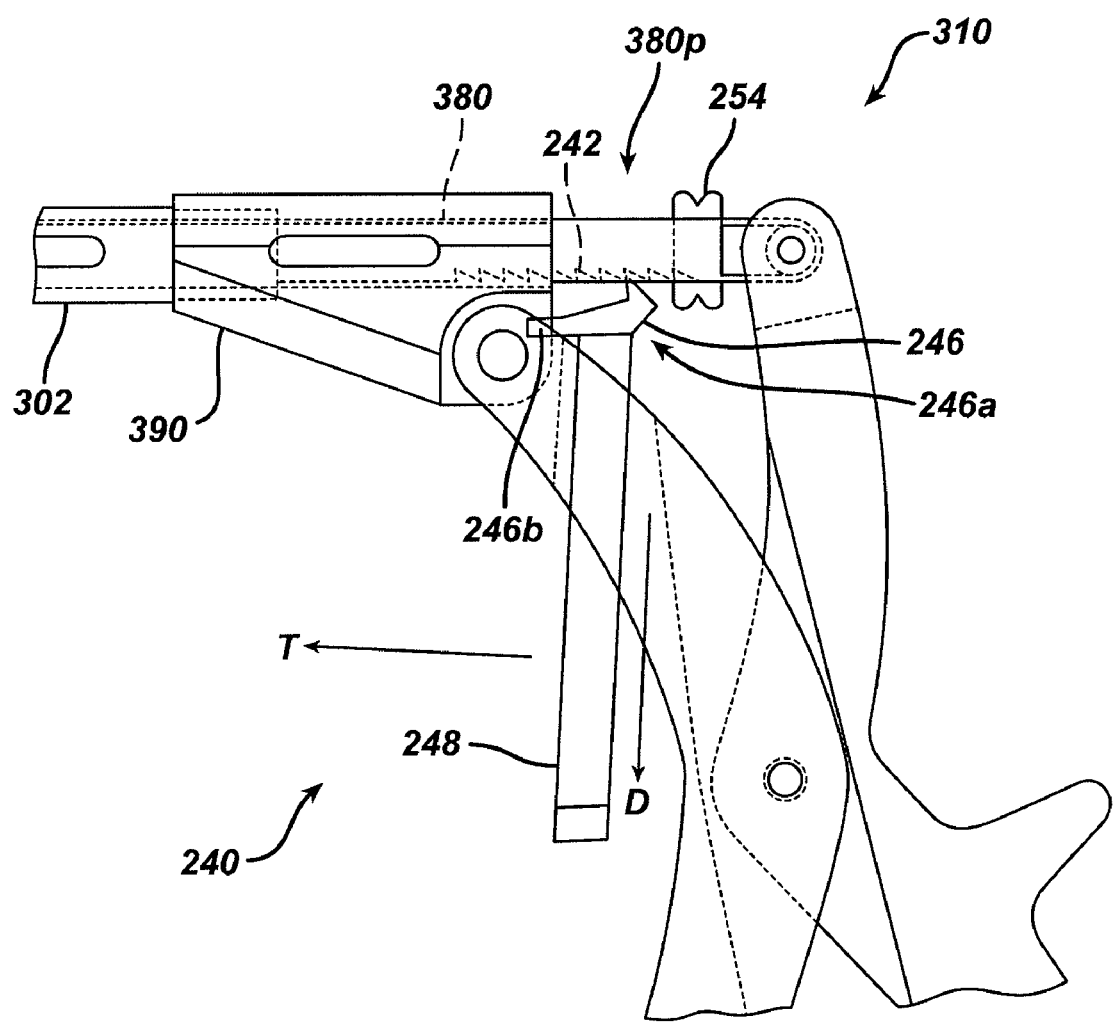
FIG. 10 is a partially transparent side view of yet another embodiment of a locking mechanism for use with a spinal rod reduction device.

FIG. 10 illustrates yet another embodiment of a locking mechanism 240 that includes a locking pawl 246 coupled to a flared portion 390 of a housing 382 and a series of notches 242 formed in a pusher member 380 of a device 310. The locking pawl 246 has a first end 246b flexibly or pivotally coupled to the housing 382 and a second, engaging end 246a for selective engagement with the series of notches 242 formed in the pusher member 380. An extension 248 can be mated to the locking pawl 246 for moving the locking pawl 246 between the engaged and disengaged positions. In the illustrated embodiment, the extension 248 is a rigid member that extends substantially perpendicular to the pusher member 380 and that is mated to the second, engaging end 246a of the locking pawl 246 such that movement of the extension 248 causes the locking pawl 246 to move between an engaged position, in which the locking pawl 246 engages the notches 242 and the pusher member 380 to maintain the pusher member 380 and a reduction member (not shown) coupled thereto in a fixed position, and a disengaged position, in which the locking pawl 246 is spaced apart from the series of notches 242 to allow the pusher member 380 and the reduction member coupled thereto to move freely. The locking pawl 246 can optionally be biased in either the engaged or disengaged position by a biasing element. While the biasing element can be any component that biases the locking pawl 246 into the engaged or disengaged position, in one embodiment the locking pawl 246 is a leaf-spring pawl that is biased in the engaged position. The locking mechanism 240 can also include a blocking mechanism adapted to prevent the locking pawl 246 from engaging the series of notches 242. In the illustrated embodiment, the blocking mechanism is a nut 254 that is threadably disposed around the proximal end 380p of the pusher member 380. The nut 254 can be moved relative to the pusher member 380 to position the nut 254 between the locking pawl 246 and the notches 242. A person skilled in the art will appreciate that, while a series of notches 242 is shown, the pusher member 380 can include a single notch.

In use, as shown in the illustrated embodiment, the locking pawl 246 is biased in the engaged position because the locking pawl 246 is a leaf-spring pawl. In order to allow movement of the pusher member 380, and in turn the reduction member 340, the extension 248 can be pulled in a direction indicated by arrow D substantially transverse to the pusher member 380 to place the locking pawl 246 in the disengaged position. In another embodiment, the extension can be pulled in a direction indicated by arrow T toward a distal end of the pusher member 380 to place the locking pawl 246 in the disengaged position. Alternatively, if the locking pawl 246 is already in the disengaged position, the extension 248 can be moved in the approximate opposite directions as described above to bias the locking pawl 246 into the engaged position. The locking pawl 246 can also be placed in the disengaged position by operating the blocking mechanism. In the illustrated embodiment, the blocking mechanism is operated by threading the nut 254 toward the distal end of the pusher member 380 in order to prevent the locking pawl 246 from engaging the series of notches 242, i.e., it places the locking pawl 246 in the disengaged position because the nut 254 is disposed between the locking pawl 246 and the series of notches 242. A person skilled in the art will appreciate that there are a number of different ways to design the blocking mechanism so that it places the locking pawl 246 in the disengaged position.

Figure 11A:
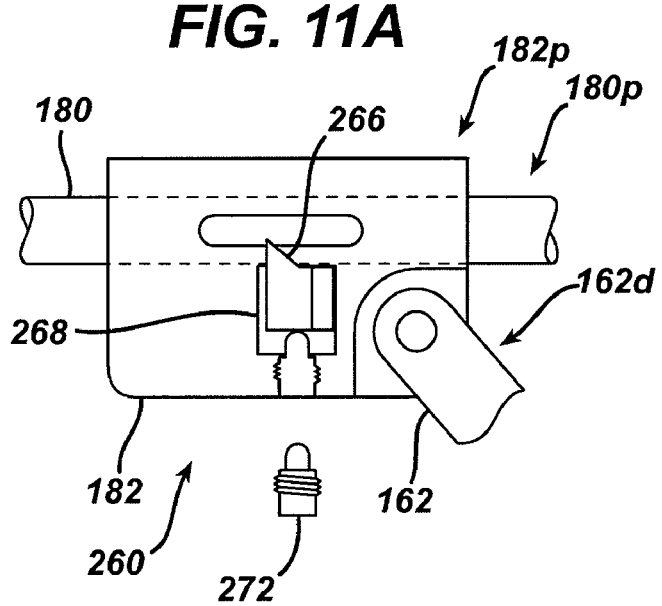
FIG. 11A is a partially transparent side view of another locking mechanism for use with a spinal rod reduction device according to another embodiment.
Figure 11B:
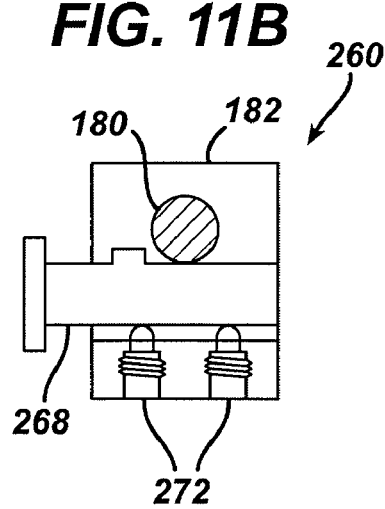
FIG. 11B is a front partially transparent view of the locking mechanism of FIG. 11A.
Figure 11C:
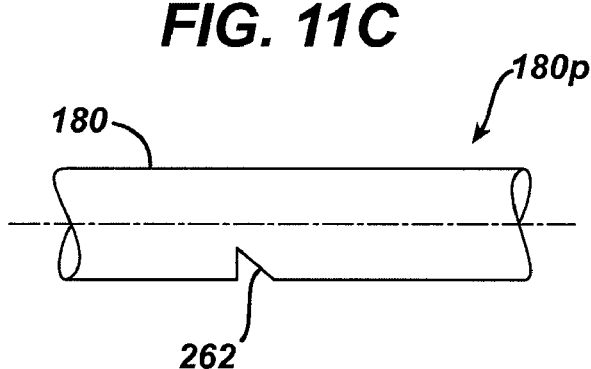
FIG. 11C is a side view of a notch on a pusher member that is part of the locking mechanism of FIGS. 11A and 11B.
Figure 11D:
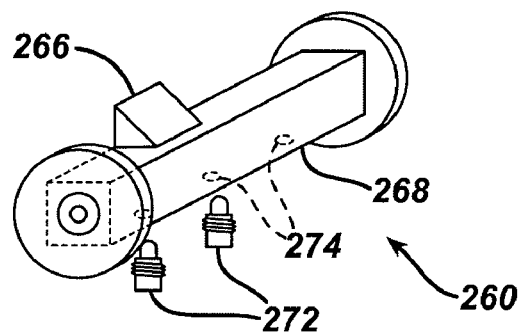
FIG. 11D is a partially transparent perspective side view of an extension that is part of the locking mechanism of FIGS. 11A and 11B.

FIGS. 11A-11D illustrate another embodiment of a locking mechanism 260 having a locking pawl 266 disposed on a bar 268 and at least one notch 262 formed in the pusher member. The bar 268 can extend through a housing 182 of a device 110 in a direction substantially transverse to a pusher member 180, and the locking pawl 266 can be formed on a portion thereof to allow the locking pawl 266 to move into and out of at least one notch 262 formed in the pusher member 180 as the bar 268 is moved relative to the housing 182. The locking mechanism 260 can further include at least one biasing mechanism adapted to bias the bar 268 toward the pusher member 180 such that the locking pawl 266 engages the notch 262 to maintain the pusher member 180 and the reduction member 140 coupled thereto in a fixed position. In one embodiment, the biasing mechanism can additionally include one or more spring members 272, such as a spring-loaded ball plunger assembly. The bar 268 can also include one or more recesses 274 on a bottom side thereof for receiving the spring members 272. When the bar 268 is moved to place the recesses 274 in alignment with the spring members 272 while the locking pawl 266 is not engaged with the pusher member 180 or notch 262, as shown in FIG. 11B, it will be held in that position by the spring members 272. As a result, the locking pawl 266 is not in contact with the notch 262. Conversely, when the bar 268 is pushed to move the recesses 274 out of alignment with the springs 272, the bar 268 is free to continue sliding transverse to the pusher member 180 until the locking pawl 266 is in alignment with pusher member 180 and notch 262. At that point, the spring members 272 are once again in alignment with recesses 274 and thus the locking pawl 266 will remain in the engaged position to prevent movement of the pusher member 180 and the reduction member 140 coupled thereto. A biasing mechanism used to bias the bar 268 toward the pusher member 180 may also allow the bar 268 to move away from the pusher member 180 far enough to permit the pawl 266 to engage the pusher member at a portion other than within the notch 262, and the pawl 266 can then snap into engagement with the notch 262 when the pusher member is actuated, such that the locking pawl 266 subsequently maintains the pusher member 180 and the reduction member 140 coupled thereto in a fixed position.

While a variety of locking mechanisms have been described herein, a person skilled in the art will appreciate that there are many different locking mechanisms that can be incorporated into the various devices disclosed herein for maintaining a reduction member in a desired fixed position. Furthermore, although various features of the described locking mechanisms have been described for particular illustrated embodiments, a person skilled in the art will appreciate that many of these components are interchangeable between the various embodiments and thus can be adapted for use in the various described embodiments, as well as in other embodiments known in the art.

A person skilled in the art will appreciate that the various methods and devices disclosed herein can be formed from a variety of materials. Moreover, particular components can be implantable and in such embodiments the components can be formed from various biocompatible materials known in the art. Exemplary biocompatible materials include, by way of non-limiting example, composite plastic materials, biocompatible metals and alloys such as stainless steel, titanium, titanium alloys and cobalt-chromium alloys, and any other material that is biologically compatible and non-toxic to the human body.

One skilled in the art will appreciate further features and advantages of the methods and devices based on the above-described embodiments. Accordingly, the methods and devices are not to be limited by what has been particularly shown and described, except as indicated by the appended claims. All publications and references cited herein are expressly incorporated herein by reference in their entirety.

What is claimed is:

1. A spinal rod reduction device, comprising:
   a fastener engaging member having first and second jaws adapted to engage at least a portion of a fastener, the first and second jaws having proximal and distal ends that are spaced a distance apart from one another, and the first and second jaws being coupled to one another at a mid-portion thereof such that movement of the proximal ends toward one another causes the distal ends of the first and second jaws to move away from one another for receiving a fastener therebetween;

a first arm fixedly coupled to the proximal end of the first jaw and offset from a longitudinal axis of the fastener engaging member;

a second arm directly and pivotally connected to the first arm;

a linkage pivotally coupled to the second arm and extending transverse to the longitudinal axis of the fastener engaging member; and a reduction member pivotally coupled to the linkage such that pivotal movement of the second arm relative to the first arm is effective to move the reduction member along the longitudinal axis of the fastener engaging member to reduce a spinal rod extending between the first and second jaws into a fastener engaged by the first and second jaws.

2. The device of claim 1, wherein the second arm is movable between an initial position in which the reduction member is positioned proximal of a distal end of the first and second jaws, and a final position in which the reduction member is positioned adjacent to the distal end of the first and second jaws.

3. The device of claim 2, wherein the linkage is adapted to be substantially aligned with the longitudinal axis of the fastener engaging member when the second arm is in the final position.

4. The device of claim 1, wherein the reduction member comprises a sleeve disposed around the first and second jaws and adapted to lock the first and second jaws in a fixed position.

5. The device of claim 1, wherein the first arm includes a proximal portion that extends substantially parallel to the longitudinal axis of the fastener engaging member, and a distal portion that extends transverse to the proximal portion and that is mated to the fastener engaging member.

6. The device of claim 1, wherein the fastener engaging member, the first arm, and the second arm define a linear pathway extending therethrough and adapted to receive a rod retainer for mating to a fastener engaged by the fastener engaging member.

7. The device of claim 1, further comprising a locking mechanism coupled to at least one of the first and second arms and effective to maintain the first and second arms in a desired fixed position relative to one another.

8. The device of claim 7, wherein the locking mechanism comprises at least one notch located on one of the first and second arms and at least one protrusion located on the other one of the first and second arms and adapted to engage the at least one notch.

9. The device of claim 7, wherein the locking mechanism is adjustable to allow the first and second arms to be maintained at a desired fixed position relative to one another.

10. The device of claim 1, wherein the reduction member comprises first and second legs.

11. The device of claim 1, wherein the first and second jaws define an opening therebetween.

12. The device of claim 1, wherein the first and second jaws include a mating element formed thereon and adapted to engage a fastener.

13. The device of claim 1, wherein the proximal end of the second jaw is detached from and freely movable relative to the first and second arms.

14. A spinal rod reduction device, comprising:

a hollow elongate member comprising first and second jaws adapted to move relative to one another to engage a fastener therebetween;

a handle immovably fixed to a proximal end of the first jaw and extending substantially parallel to and offset from a longitudinal axis of the hollow elongate member, a proximal end of the second jaw being freely movable relative to the handle and the proximal end of the first jaw;

a reduction member slidably coupled to the hollow elongate member and adapted to distally advance a spinal rod extending between the first and second jaws into the fastener engaged by the first and second jaws; and a linkage assembly pivotally coupled to the handle and the reduction member and adapted to advance the reduction member relative to the first and second jaws.

15. The device of claim 14, wherein the reduction member comprises a sleeve disposed around the hollow elongate member and movable between an initial position in which a distal end of the first and second jaws are free to flex relative to one another to receive a fastener therebetween, and a final position in which the distal end of the first and second jaws are locked in a fixed position relative to one another to engage a fastener therebetween.

16. The device of claim 14, wherein at least a portion of the linkage assembly extends transverse to the longitudinal axis of the hollow elongate member in a first position, and extends substantially parallel to the longitudinal axis of the hollow elongate member in a second position.

17. The device of claim 14, wherein the linkage assembly comprises an actuator pivotally coupled to the handle and at least one linkage extending between the actuator and the reduction member.

18. The device of claim 14, further comprising a locking mechanism coupled to the handle and effective to maintain the reduction member in a desired fixed position relative to the hollow elongate member.

19. The device of claim 14, wherein at least one of the first and second jaws has a proximal extension adapted to move the first and second jaws apart.

20. A method for reducing a spinal rod into a bone anchor, comprising:

moving proximal ends of first and second jaws of a fastener engaging member toward one another to cause distal ends of the first and second jaws to move away from one another;

positioning a fastener between the first and second jaws formed on the fastener engaging member; and pivoting a movable arm toward an unmovable arm offset from a longitudinal axis of the fastener engaging member and fixedly mated to the fastener engaging member to pivot a linkage coupled to the movable arm from a first position in which the linkage extends transverse to the longitudinal axis of the fastener engaging member, to a second position in which the linkage extends substantially parallel to the longitudinal axis of the fastener engaging member, the linkage advancing a reduction member toward the fastener as the linkage moves from the first position to the second position to advance a spinal rod extending between the opposed jaws into the fastener.

21. The method of claim 20, wherein, when the movable arm is pivoted toward the unmovable arm, the reduction member is advanced over the first and second jaws into a locked position to lock the distal ends of the first and second jaws in a fixed position relative to one another to thereby engage the fastener between the first and second jaws.

22. The method of claim 20, further comprising delivering a rod retainer through a pathway extending through the fastener engaging member, and applying the rod retainer to the fastener to lock the spinal rod in the fastener.

23. The method of claim 22, wherein the pathway comprises a linear pathway extending between the movable arm and the unmovable arm and extending through the fastener engaging member.

24. The method of claim 20, wherein the movable arm is maintained in the second position by a locking mechanism that extends between the movable arm and the unmovable arm.

25. The method of claim 20, wherein the fastener comprises a bone screw that is disposed in a vertebra.

* * * * *

UNITED STATES PATENT AND TRADEMARK OFFICE
CERTIFICATE OF CORRECTION

| | | |
|---|---|---|
| PATENT NO. | : 7,887,541 B2 | Page 1 of 1 |
| APPLICATION NO. | : 11/828652 | |
| DATED | : February 15, 2011 | |
| INVENTOR(S) | : Runco et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 175 days.

Signed and Sealed this
Twenty-sixth Day of July, 2011

David J. Kappos
*Director of the United States Patent and Trademark Office*